United States Patent
Gaston et al.

(10) Patent No.: US 12,083,089 B2
(45) Date of Patent: *Sep. 10, 2024

(54) COMPOSITIONS AND METHODS FOR STIMULATING VENTILATORY AND/OR RESPIRATORY DRIVE

(71) Applicant: CASE WESTERN RESERVE UNIVERSITY, Cleveland, OH (US)

(72) Inventors: Benjamin M. Gaston, Indianapolis, IN (US); Stephen J. Lewis, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 32 days.

This patent is subject to a terminal disclaimer.

(21) Appl. No.: 17/742,040

(22) Filed: May 11, 2022

(65) Prior Publication Data

US 2022/0273604 A1 Sep. 1, 2022
US 2024/0139140 A9 May 2, 2024

Related U.S. Application Data

(63) Continuation-in-part of application No. 17/141,999, filed on Jan. 5, 2021, which is a continuation of
(Continued)

(51) Int. Cl.
*A61K 31/225* (2006.01)
*A61K 9/00* (2006.01)
(Continued)

(52) U.S. Cl.
CPC .......... *A61K 31/225* (2013.01); *A61K 9/0019* (2013.01); *A61K 45/06* (2013.01)

(58) Field of Classification Search
CPC .... A61K 31/225; A61K 9/0019; A61K 45/06; A61K 31/24; A61K 31/485; A61K 2300/00
See application file for complete search history.

(56) References Cited

U.S. PATENT DOCUMENTS 6,242,573 B1    6/2001 Goto et al.
10,080,732 B2 * 9/2018 Gaston ................. A61K 31/225
(Continued)

FOREIGN PATENT DOCUMENTS

WO      1992/204024 A2    3/1992
WO      WO-2016115245 A1 *  7/2016    ........... A61K 31/225

OTHER PUBLICATIONS

"Clinical implications of opioid-induced ventilatory impairment", Anaesth Intensive Care, 50, pp. 52-67 (2022) by Pattullo (Year: 2022).*
(Continued)

*Primary Examiner* — Jeffrey S Lundgren
*Assistant Examiner* — Alexander K. Showalter
(74) *Attorney, Agent, or Firm* — Tarolli, Sundheim, Covell & Tummino LLP

(57) ABSTRACT

A method of attenuating opioid induced ventilatory and/or respiratory depression and/or augmenting opioid induced analgesia in a subject in need thereof includes administering
(Continued)

to the subject a therapeutically effective amount of a composition comprising a cystine ester or an adduct, a pharmaceutically acceptable salt, a tautomer, or a solvate thereof.

16 Claims, 16 Drawing Sheets

Related U.S. Application Data application No. 16/515,355, filed on Jul. 18, 2019, now Pat. No. 10,881,633, which is a continuation-in-part of application No. 16/139,937, filed on Sep. 24, 2018, now Pat. No. 10,543,187, which is a continuation of application No. 15/543,524, filed as application No. PCT/US2016/013241 on Jan. 13, 2016, now Pat. No. 10,080,732.

(60) Provisional application No. 63/187,094, filed on May 11, 2021, provisional application No. 62/102,902, filed on Jan. 13, 2015.

(51) Int. Cl.
*A61K 45/06* (2006.01)
*A61K 31/24* (2006.01)
*A61K 31/485* (2006.01)

(56) References Cited

U.S. PATENT DOCUMENTS

| 2002/0115723 A1 | 8/2002 | Iwasaki et al. |
| 2002/0137785 A1 | 9/2002 | Kindness et al. |
| 2013/0131028 A1 | 5/2013 | Snyder et al. |
| 2013/0338225 A1 | 12/2013 | Ward et al. |

OTHER PUBLICATIONS

"Continuous intravenous infusion of opioid drugs", Med Clin North Am., 71(2), pp. 233-241 (1987) by Portenoy (Year: 1987).*

Mendoza et al., l-Cysteine ethyl ester reverses the deleterious effects of morphine on, arterial blood-gas chemistry in tracheotomized rats, Resp. Physiol. Neurobiol., 189, pp. 136-143 (Year: 2013).*

Gupta, et al., Feb. 2018 (https://www.apsf.org/newsletter/february-2018/).

Applicant: Case Western Reserve University; Compositions and Methods for Stimulating Ventilatory and/or Respiratory Drive; International Application No. PCT/US2016/013241; PCT International Filing Date: Jan. 13, 2016; International Search Report and Written Opinion; Feb. 28, 2016; 6 pgs.

Mendoza et al. (Respir Physiol Neurobiol. (2013) 189(1): 136-143.

* cited by examiner

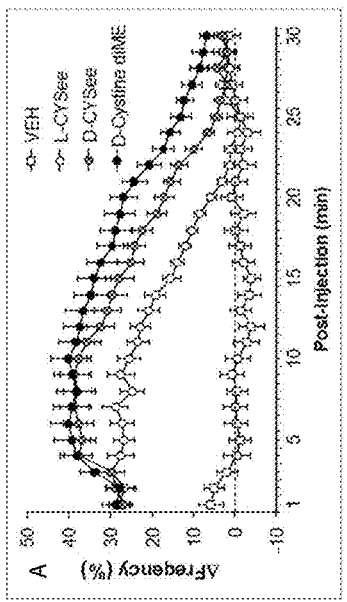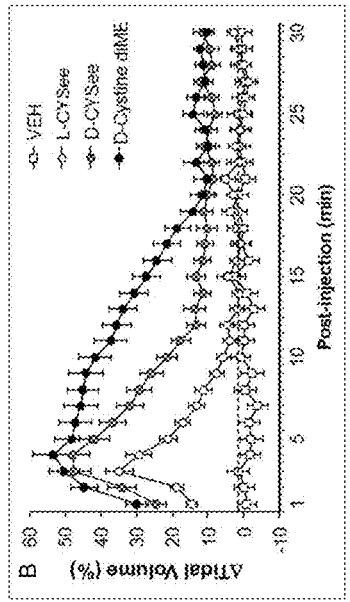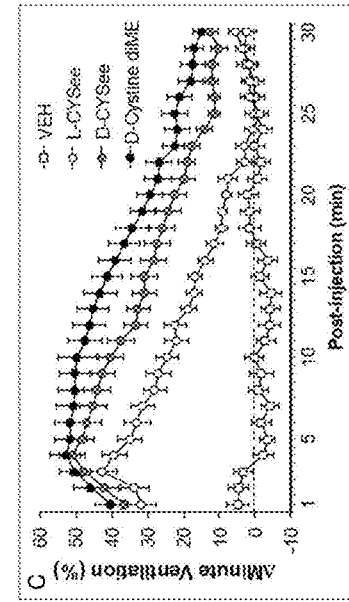

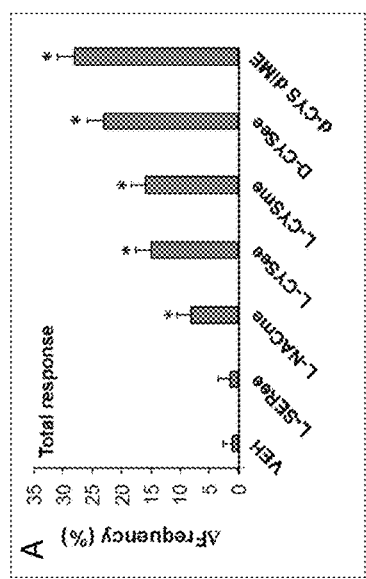 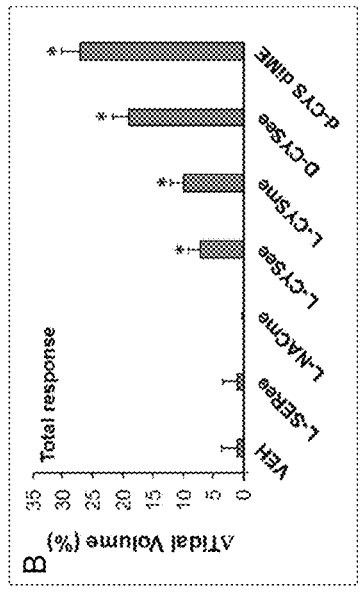 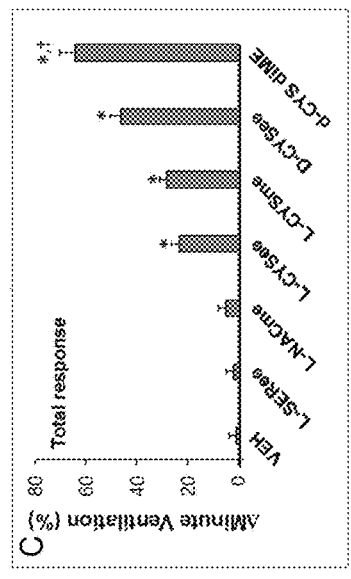

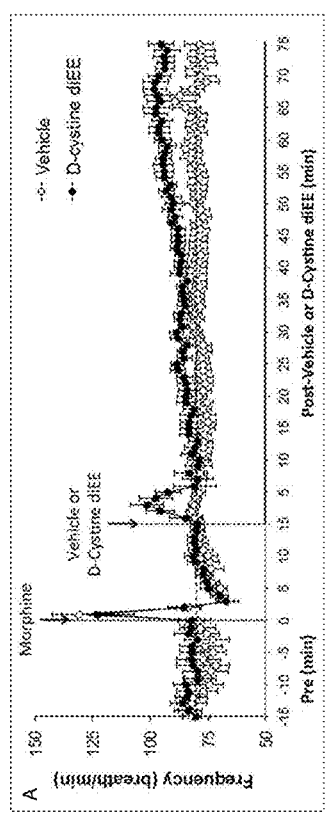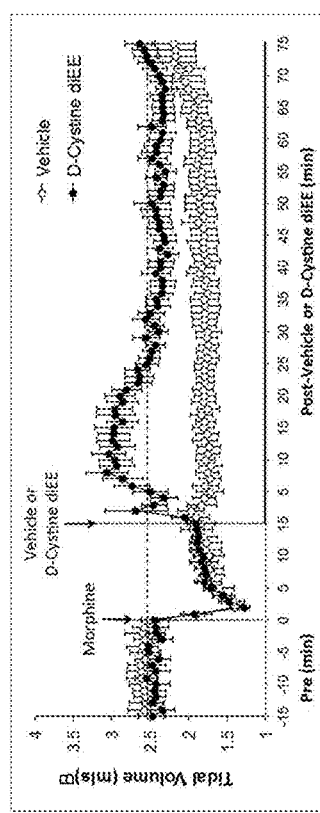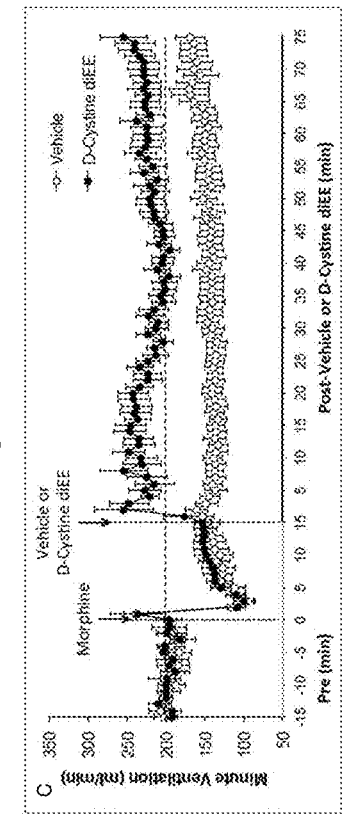
Fig. 5A
Fig. 5B
Fig. 5C
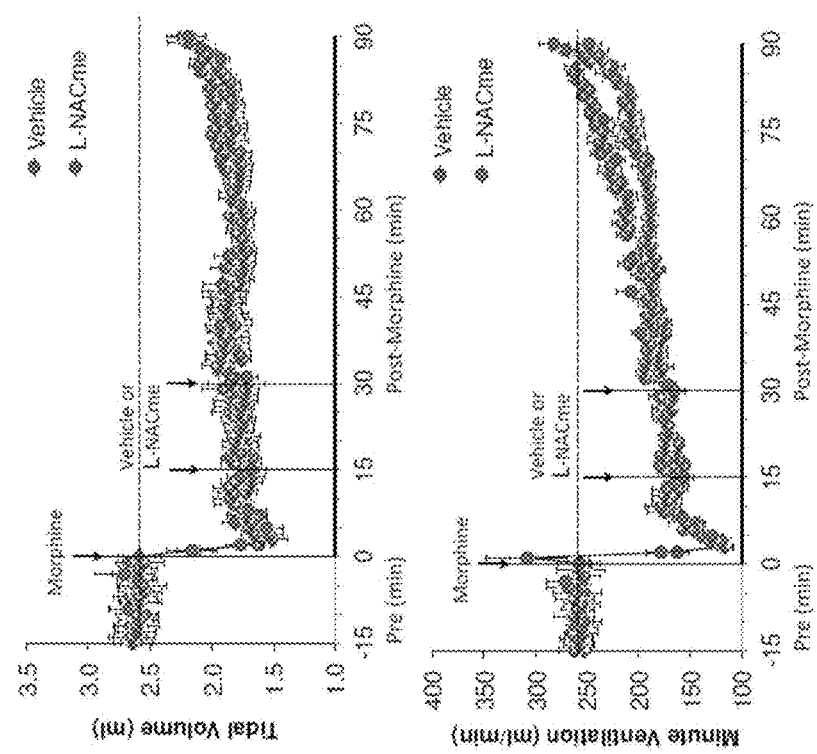
Fig. 23 (Continued)

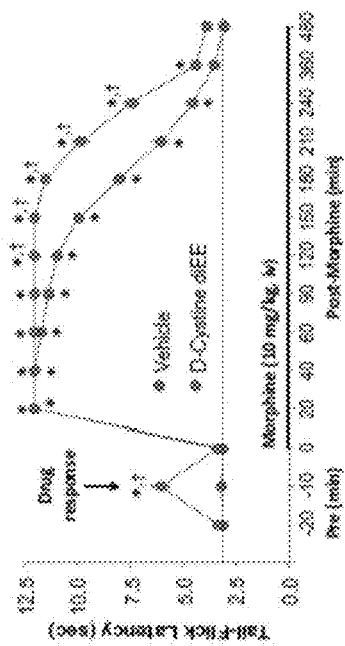
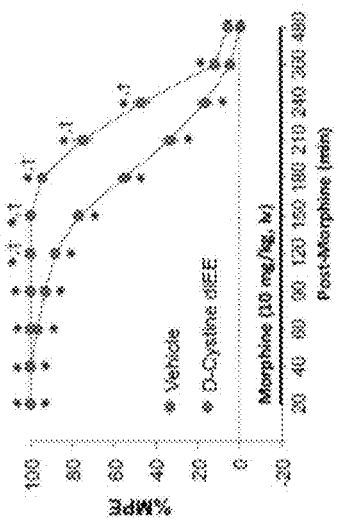
Fig. 20
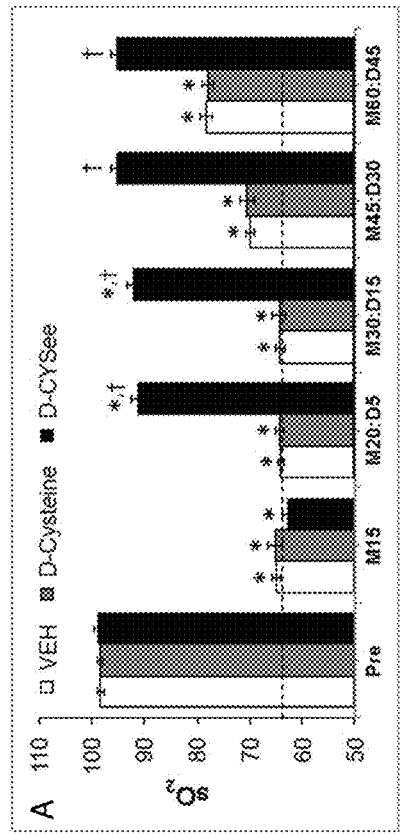
Fig. 8A
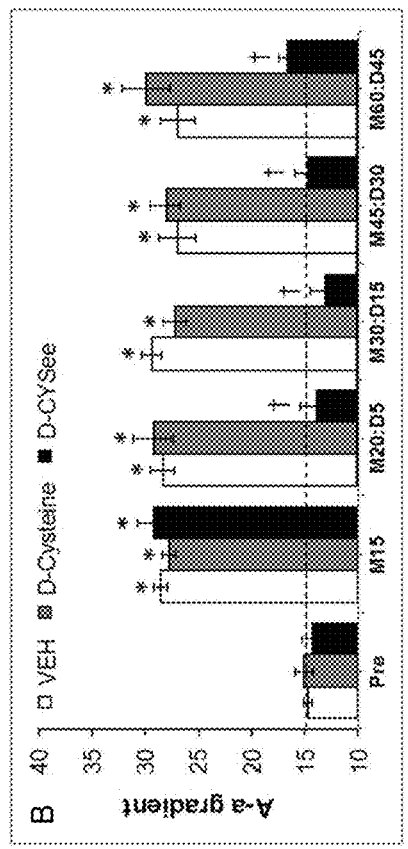
Fig. 8B

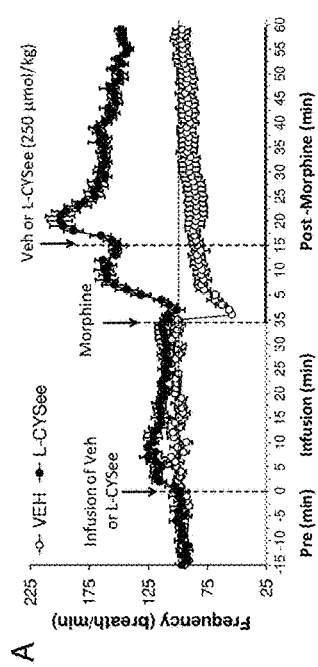
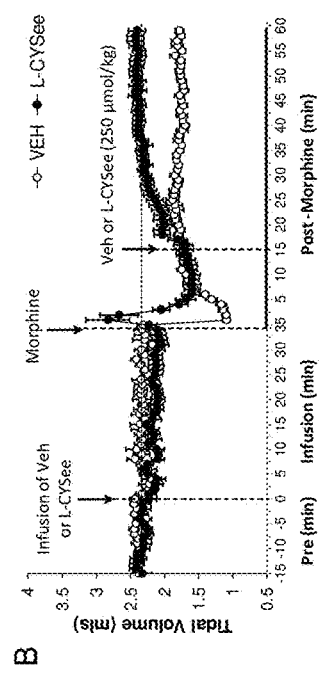
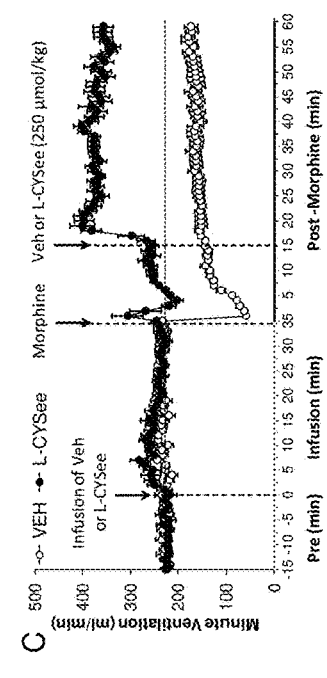
Fig. 9A
Fig. 9B
Fig. 9C
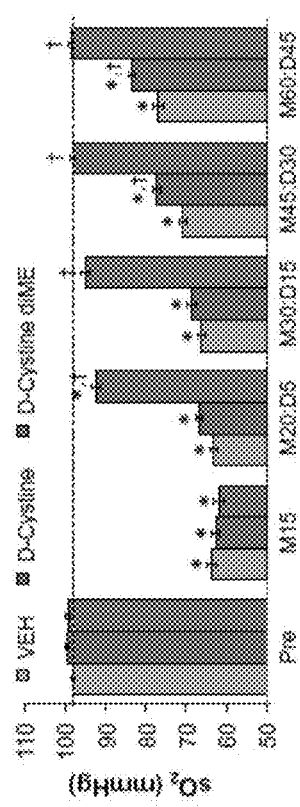
Fig. 18 (Continued)
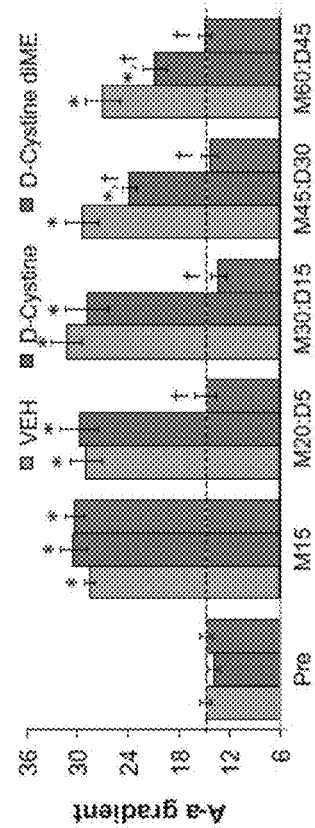
Fig. 19

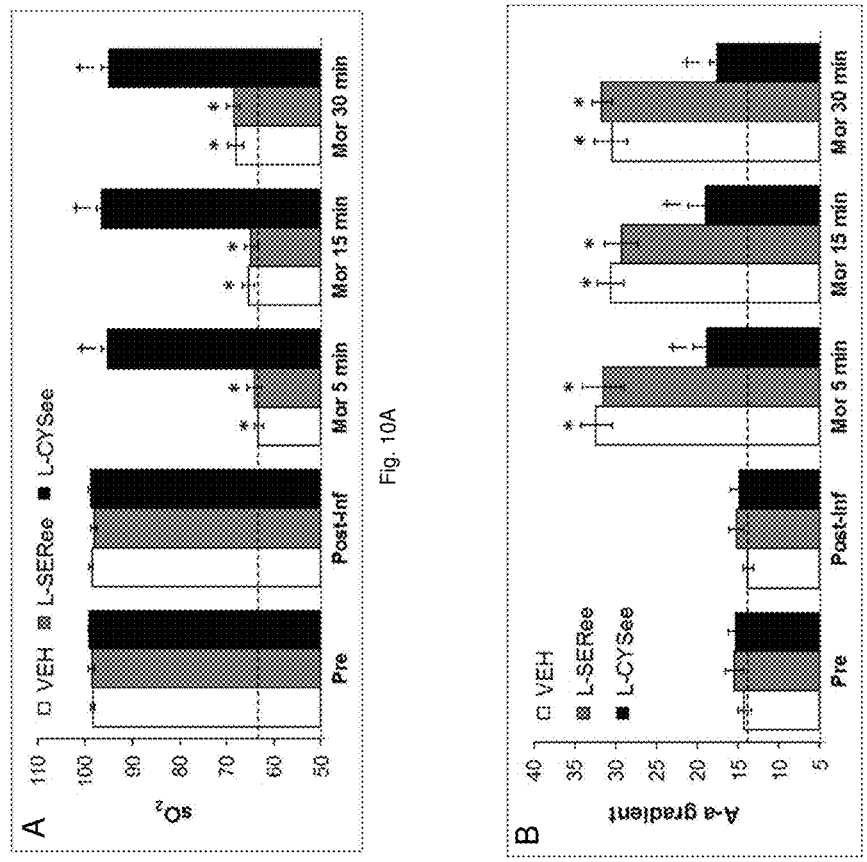
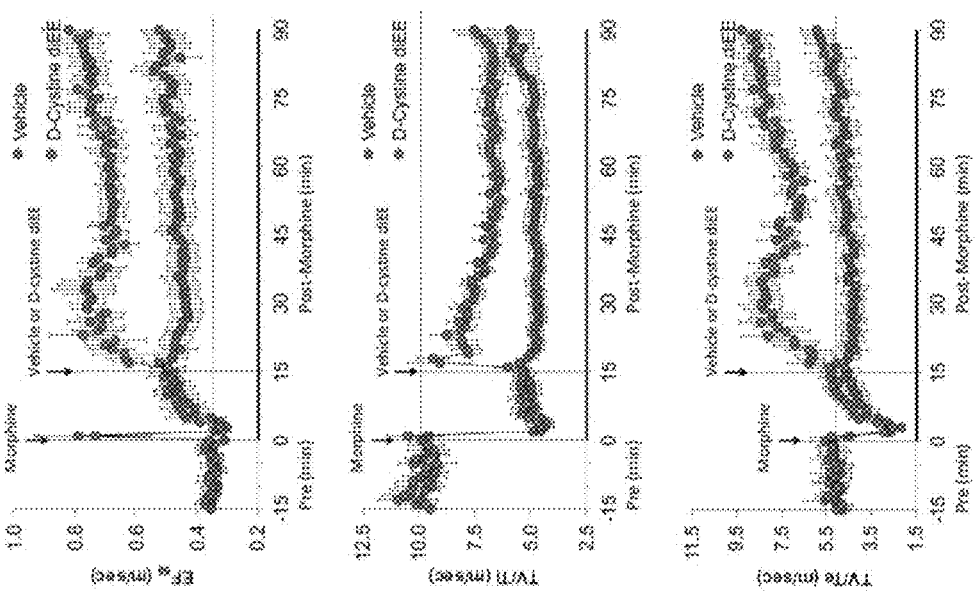

COMPOSITIONS AND METHODS FOR STIMULATING VENTILATORY AND/OR RESPIRATORY DRIVE

RELATED APPLICATION

This application claims priority from U.S. Provisional Application No. 63/187,094, filed May 11, 2021, this application is also a Continuation-In-Part of U.S. patent application Ser. No. 17/141,999, filed Jan. 5, 2021, which is a Continuation of U.S. patent application Ser. No. 16/515,355, filed Jul. 18, 2019, which is a Continuation-in-Part of U.S. Ser. No. 16/139,937, filed Sep. 24, 2018, which is a Continuation of U.S. Ser. No. 15/543,524, filed Jul. 13, 2017, which is a National Phase Filing of PCT/US2016/013241, which claims priority from U.S. Provisional Application No. 62/102,902, filed Jan. 13, 2016, the subject matter of which are incorporated herein by reference in their entirety.

TECHNICAL FIELD

Embodiments described herein relate to compositions and methods of stimulating ventilatory and/or respiratory drive in a subject in need thereof, and particularly relates to compositions and methods of treating breathing diseases and/or disorders associated with impaired ventilatory and/or respiratory drive.

BACKGROUND

Normal control of breathing is a complex process that involves the body's interpretation and response to chemical stimuli, such as carbon dioxide, pH and oxygen levels in blood, tissues and the brain. Breathing control is also affected by wakefulness (i.e., whether the patient is awake or sleeping). Within the brain medulla there are respiratory control centers that interpret the various signals that affect respiration and issue commands to muscles that perform the work of breathing. Key muscle groups are located in the abdomen, diaphragm, larynx, pharynx and thorax. Sensors located centrally and peripherally provide input to the brain's central respiration control areas that enable response to changing oxygen requirements.

Normal respiratory rhythm is maintained primarily by the body's rapid response to changes in carbon dioxide levels ($CO_2$). Increased $CO_2$ levels signal the body to increase breathing rate and depth resulting in higher oxygen levels and subsequent lower $CO_2$ levels. Conversely, low $CO_2$ levels can result in periods of apnea (no breathing) since the stimulation to breathe is absent. This is what happens when a person hyperventilates. Additionally, low blood oxygen levels stimulate respiratory drive, and this mechanism can become the primary driver in patients with chronically high $PCO_2$ levels.

Impaired ventilatory drive can complicate a broad spectrum of diseases in pulmonary, sleep, and critical care medicine. Patients with various forms of chronic obstructive pulmonary disease (COPD)—among which can be considered late-stage cystic fibrosis (CF)—can have impaired ventilatory responses when treated with oxygen or narcotics. In obstructive sleep apnea (OSA), intermittent hypoxia associated with impaired short- and long-term facilitation of hypoxic ventilatory drive and with loop gain may predispose to perioperative complications and adverse neurocognitive sequelae. A variety of other conditions with components of disordered ventilatory control—ranging from congestive heart failure (CHF) to Arnold-Chiari malformation—can only be managed with mechanical ventilation. Additionally, endotracheally-intubated patients in the critical care setting who require narcotics for pain control can become unmanageable if narcotic use is stopped, but can fail extubation because of respiratory depression if the narcotic is continued. These pulmonary and critical care issues can be all the more challenging in patients with underlying COPD, CF, CHF, OSA and other conditions affecting ventilatory drive.

Few medications are effective as respiratory stimulants. Methylxanthines can be effective in patients with apnea of prematurity, but are often ineffective in older patients. Almitrine can transiently improve ventilatory drive in adults with COPD. However, the administration of almitrine is associated with the development of pulmonary arterial hypertension and peripheral neuropathy; and it does not affect outcome.

Conditions associated with impaired ventilatory drive are common and have a substantial public health impact. For example, large, population-based studies report a prevalence of moderate-severe obstructive sleep apnea of 2-14% of the American population—depending on age and gender—and prevalence may be higher (up to 38% of men) in pulmonary clinic. A significant proportion of patients with OSA have impaired ventilatory drive, particularly those who also have heart failure. There is a large, unmet need for a safe and effective respiratory stimulant in pulmonary and critical care medicine.

Additionally, commonly used narcotic and benzodiazepine medications suppress ventilatory drive. Specifically, they depress the slope of the relationship between $PCO_2$ and minute ventilation. This is a major issue in several important settings. In the operating room and post-anesthesia care setting, patients may have prolonged respiratory depression associated with pain control. This results in prolonged hospitalizations or early, risky discharge and death. In the chronic pain population—in the Veteran's Administration system, for example—death from nocturnal respiratory depression is at epidemic proportions among patients on chronic opiate therapy. Opiate addiction is also at epidemic levels, and hundreds of young people die annually without an effective emergency respiratory stimulant. On the battlefield, medics can have to choose between excruciating pain and risk of death from respiratory depression. In the Intensive Care population, physicians often have to choose between the risk of being on the ventilator for one or more days and the risk of awaking a patient in pain and distress. This is a problem in patients with a baseline blunted $CO_2$ response, such as patients with severe COPD, CF or other obstructive lung disease. Emergency treatment for narcotic-induced respiratory depression is limited largely to the use of narcotic antagonists, such as naloxone, which are effective at reversing the narcotic induced respiratory depression but also reverse the narcotic mediated pain control, exacerbating the original problem. Further, this treatment is specific to narcotics and is ineffective for benzodiazepine or other sedative or anesthetic induced respiratory depression. A respiratory stimulant that overcomes respiratory depression from any source is needed to address these needs.

SUMMARY

Embodiments described herein relate to compositions and methods of attenuating and/or treating opioid induced ventilatory and/or respiratory depression in a subject in need thereof, and particularly relates to the use of thiol-based compounds in compositions and methods of treating ventilatory and/or respiratory depression in a subject in need thereof. It was found that administration of thiol-based compounds described herein markedly attenuated the ventilatory and/or respiratory depressant effects elicited by opioids, such as morphine or fentanyl, while augmenting opioid-induced analgesia.

In some embodiments, the methods can include attenuating opioid induced ventilatory and/or respiratory depression in a subject in need thereof by administering to the subject a therapeutically effective amount of a composition comprising a cystine ester or an adduct, a pharmaceutically acceptable salt, a tautomer, or a solvate thereof.

In some embodiments, the opioid administration elicits disturbances in ventilatory parameters (e.g., decreases in frequency of breathing, tidal volume, and minute ventilation), Arterial Blood Gas (ABG) chemistry (e.g., decreases in pH, $pO_2$, $sO_2$ with increases in $pCO_2$) and Alveolar-arterial (A-a) gradient while causing sedation and analgesia.

In other embodiments, administration of the therapeutically effective amount of the composition is effective to elicit sustained reversal of opioid elicited disturbances in ventilatory parameters (e.g., decreases in frequency of breathing, tidal volume, and minute ventilation), Arterial Blood Gas (ABG) chemistry (e.g., decreases in pH, $pO_2$, $sO_2$ with increases in pCO2) and Alveolar-arterial (A-a) gradient while maintaining or augmenting opioid sedation and analgesia.

The composition can be administered to the subject systemically by, for example, topical (e.g., inhalation), enteral (e.g., oral), and/or parenteral (e.g., intravenous injection) administration.

In some embodiments, the composition is administered concurrently with opioid administration and/or up to about 10 minutes, up to about 20 minutes, up to about 30 minutes, up to about 40 minutes, up to about 50 minutes, up to about 60 minutes, up to about 70 minutes, up to about 80 minutes, up to about 90 minutes, up to about 100 minutes, up to about 110 minutes, or up to about 120 minutes before or after initiation of opioid administration.

In some embodiments, the cystine ester can have the formula:

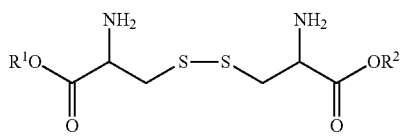

where $R^1$ and $R^2$ are the same or different and are selected from the group consisting of H, unsubstituted or substituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl, and heterocyclyl containing from 5-14 ring atoms, and at least one of $R^1$ and $R^2$ is not a H; or an adduct, a pharmaceutically acceptable salt, a tautomer, or a solvate thereof.

In some embodiments, $R^1$ and $R^2$ are independently H or an unsubstituted or substituted $C_1$-$C_{24}$ alkyl, and at least one of $R^1$ and $R^2$ is not a H. In other embodiments, $R^1$ and $R^2$ are independently selected from the group consisting of H, methyl, ethyl, propyl, and butyl, and at least one of $R^1$ and $R^2$ is not a H.

In other embodiments, the cystine ester can be a cystine dialkyl ester, or an adduct, a pharmaceutically acceptable salt, a tautomer, or a solvate thereof. The cystine dialkyl ester can be selected from cystine dimethyl ester, cystine diethyl ester, combinations thereof, or an adduct, a pharmaceutically acceptable salt, a tautomer, or a solvate thereof.

In still other embodiments, the cystine dialkyl ester can be a D-cystine dialkyl ester or an adduct, a pharmaceutically acceptable salt, a tautomer, or a solvate thereof. For example, the D-cystine dialkyl ester can be a D-cystine dimethyl ester, D-cystine diethyl ester, or an adduct, a pharmaceutically acceptable salt, a tautomer, or a solvate thereof.

In still other embodiment, the adduct of the cystine dialkyl ester can be a biologically active adduct and include at least one of an albumin adduct, a glucose adduct, an L-cysteine adduct, an L-glutathione adduct, and/or an S-nitroso adduct.

In other embodiments, the composition can be administered to the subject at an amount effective to prevent the need for mechanical ventilation in subjects with acutely impaired ventilatory and/or respiratory drive because of an acute requirement for narcotic analgesia.

In still other embodiments, the composition can be administered to a subject in combination with at least one additional therapeutic agent that changes normal breathing in a subject. The additional agent can be selected from the group consisting of an opioid, doxapram and enantiomers thereof, acetazolamide, almitrine, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In yet another embodiment, the composition and the agent are separately administered to the subject. In yet another embodiment, the compound and the agent are co-administered to the subject.

Still other embodiments described herein relate to a composition that includes an opioid capable of inducing ventilatory and/or respiratory depression in a subject and an amount of cystine ester effective to attenuate the opioid induced ventilatory and/or respiratory depression and augment opioid-induced analgesia when the composition is administered to the subject.

In some embodiments, the opioid can include at least one of alfentanil, buprenorphine, butorphanol, carfentanil, codeine, diamorphine, dextromoramide, dezocine, dihydrocodeine, fentanyl, hydrocodone, hydromorphone, levorphanol, meperidine, meptazinol, methadone, morphine, nalbuphine, nalorphine, opium, oxycodone, oxymorphone, pentazocine, propoxyphene, remifentanil, sufentanil, tapentadol, and tramadol, and pharmaceutically acceptable salts thereof. For example, the opioid can be carfentanil, fentanyl, remifentanil, or sufentanil.

BRIEF DESCRIPTION OF THE DRAWINGS

FIGS. 1(A-C) illustrate plots showing the ventilatory responses elicited by vehicle (saline) and test compounds (500 mol/kg, i.v.) in conscious rats. Each drug was given to a separate group of rats (n=8 per group). Data are presented as mean±SEM.

FIGS. 8(A-B) illustrate graphs showing the effects of D-Cysteine (500 μmol/kg, i.v.) and D-CYSee (500 μmol/kg, i.v.) on arterial blood-gas chemistry and A-a gradients in rats which had received an injection of morphine (10 mg/kg, i.v.). Data are presented mean±SEM (n=9 rats per group). *$P<0.05$, difference from pre-values. †$P<0.05$, D-Cysteine or D-CYSee versus vehicle.

FIGS. 10(A-B) illustrate graphs showing the effects of prior infusion of L-SERee or L-CYSee (total dose of 500 μmol/kg, i.v.) on changes in arterial blood-gas chemistry and A-a gradient elicited by morphine (10 mg/kg, i.v.) in conscious rats. Data are presented mean±SEM (n=9 rats per group). *$P<0.05$, difference from pre-values. †$P<0.05$, L-SERee or L-CYSee versus vehicle.

FIG. 17 illustrates plots showing changes in EF50 (top panel), inspiratory drive (TV/Ti) (middle panel) and expiratory drive (TV/Te) (bottom panel) in freely moving rats upon (a) injection of morphine (10 mg/kg, IV) and subsequent injection of vehicle (saline) or d-cystine diethyl ester (d-cystine diEE, 500 μmol/kg, IV). The data are presented as mean±SEM. There were 9 rats in each group.

FIG. 19 illustrates graphs showing changes in A-a gradient elicited by an injection of morphine (10 mg/kg, IV) in 3 separate groups of freely moving rats followed by injection of vehicle (VEH, saline), d-Cystine (500 μmol/kg, IV) or d-cystine dimethyl ester (d-cystine diME, 500 μmol/kg, IV). M15-M60, 15-60 min after injection of morphine. D5-D45, 5-45 min after injection of drug (vehicle, d-Cystine or d-cystine diME). The data are shown as mean±SEM. There were 9 rats in each group. *$P<0.05$, significant change from Pre-values. †$P<0.05$, d-cystine diEE versus vehicle.

FIG. 21 illustrates graphs showing: top panel: Peak percent changes in ventilatory parameters elicited by injection of vehicle or D-cystine diethyl ester (D-cystine diEE, 500 mol/kg, IV) in separate groups of morphine (10 mg/kg, IV)-treated rats. Bottom panel: Total percent changes in ventilatory parameters elicited by injection of vehicle or D-cystine diethyl ester (D-cystine diEE, 500 mol/kg, IV) in separate groups of morphine (10 mg/kg, IV)-treated rats. The data are shown as mean±SEM. There were 9 rats in each group. *P<0.05, significant change from Pre-values. †P<0.05, D-cystine diEE versus vehicle.

DETAILED DESCRIPTION

Figure 3A:
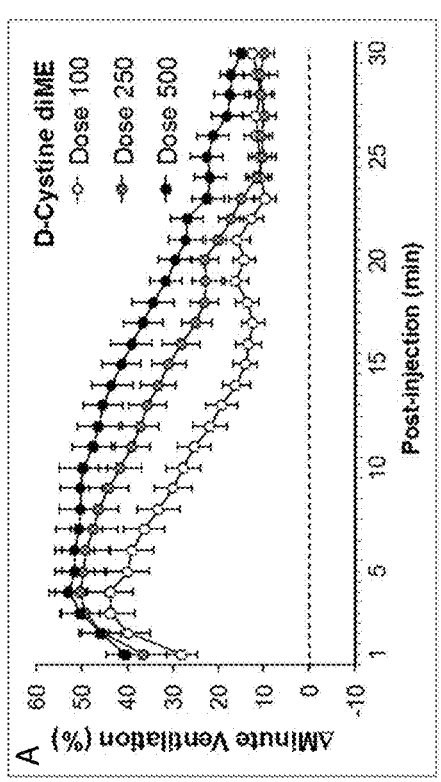
FIGS. 3(A-B) illustrate plots showing dose-dependent changes in ventilatory parameters elicited by D-Cystine diME in conscious rats. Each dose was given to a separate group of rats (n=8 rats per group). The data are presented as mean±SEM.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.," as used herein are non-limiting and are for illustrative purposes only. "Including" and "including but not limited to" are used interchangeably.

The term "or" as used herein should be understood to mean "and/or", unless the context clearly indicates otherwise.

The term "about" or "approximately" as used herein refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore, can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, e.g., sulfoxides or sulfinimides, is likewise termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refers to diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" refers to a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "apnea" refers to the absence of normal breathing resulting in intermittent stoppages of breathing.

The term "Cheyne-Stokes respiration" refers to a specific pattern of breathing characterized by a crescendo pattern of breathing that results in apneas and/or hypopneas. A hallmark of this condition is that breathing becomes out of phase with blood oxygen levels.

The term "patency" refers to the state or condition of an airway being open or unblocked.

The term "hypopnea" is similar in many respects to apnea; however, breathing does not fully stop but is partially stopped (i.e., less than 100% of normal breathing, but more than 0% of normal breathing). Hypopnea is also referred to herein as "partial apnea" and can be subdivided into obstructive, central or mixed types.

The term "hypoxia" refers to a deficiency in the amount of oxygen, being taken in by an organism, as well as to a deficiency in the amount of oxygen, which is transported to tissues in an organism.

The term "normoxia" refers to a homoeostasis or "normal condition" regarding the amount of oxygen being taken in by an organism, as well as to a homeostasis or "normal condition" with respect to the amount of oxygen which is transported to tissues in an organism.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In some embodiments, the compound or active ingredient is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials, which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, 3$^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Tautomerizations can be catalyzed by: Base: 1. deprotonation; 2. formation of a delocalized anion (e.g., an enolate);

3. protonation at a different position of the anion; Acid: 1. protonation; 2. formation of a delocalized cation; 3. deprotonation at a different position adjacent to the cation.

A "patient," "subject," or "host" to be treated by the compounds or methods described herein may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compounds. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament", "active ingredient", and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_1$-6 alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_1$-6 alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, acylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{ao}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—

O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COOH), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (–$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The term "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

Embodiments described herein relate to compositions and methods of attenuating and/or treating opioid induced ventilatory and/or respiratory depression in a subject in need thereof, and particularly relates to the use of thiol-based compounds in compositions and methods of treating ventilatory and/or respiratory depression in a subject in need thereof. It was found that administration of thiol-based compounds described herein markedly attenuated the ventilatory and/or respiratory depressant effects elicited by opioids, such as morphine or fentanyl, while augmenting opioid induced analgesia.

In some embodiments, the methods can include attenuating opioid induced ventilatory and/or respiratory depression in a subject in need thereof by administering to the subject a therapeutically effective amount of a composition comprising a cystine ester or an adduct, a pharmaceutically acceptable salt, a tautomer, or a solvate thereof.

It was found that cystine esters, such as cystine alkyl esters (e.g., cystine dialkyl ester, cystine dimethyl ester or cystine diethyl ester) are potent stimulants of ventilatory and/or respiratory drive that effectively overcome breathing disorders, such as narcotic or opioid induced respiratory depression. Advantageously, cystine esters described herein can stimulate respiratory drive and overcome respiratory opioid induced respiratory depression in a subject in need thereof while augmenting opioid induced analgesia in the subject.

In some embodiments, the cystine ester can have the formula:

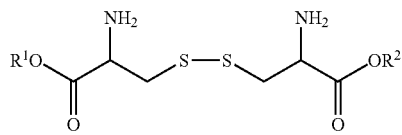

where $R^1$ and $R^2$ are the same or different and are selected from the group consisting of H, unsubstituted or substituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), heteroaryl containing from 5-14 ring atoms, (wherein from 1-6 of the ring atoms is independently selected from N, NH, N($C_1$-$C_3$ alkyl), O, and S), and heterocyclyl containing from 5-14 ring atoms (wherein from 1-6 of the ring atoms is independently selected from N, NH, N($C_1$-$C_3$ alkyl), O, and S), and at least one of $R^1$ and $R^2$ is not a H; or an adduct, a pharmaceutically acceptable salt, a tautomer, or a solvate thereof.

In some embodiments, $R^1$ and $R^2$ are independently H or an unsubstituted or substituted $C_1$-$C_{24}$ alkyl, wherein at least one of $R^1$ and $R^2$ is not a H. In other embodiments, $R^1$ and $R^2$ are independently selected from the group consisting of H, methyl, ethyl, propyl, and butyl, and at least one of $R^1$ and $R^2$ is not a H.

In other embodiments, the cystine ester can be a cystine dialkyl ester, or an adduct, a pharmaceutically acceptable salt, a tautomer, or a solvate thereof. The cystine dialkyl ester can comprise a mixture at least one of D or L isomers of a cystine dialkyl ester. For example, the cystine dialkyl ester can comprise a mixture of: less than about 50% by weight of the D isomer of a cystine dialkyl ester and greater than about 50% by weight of the L isomer of a cystine dialkyl ester, less than about 25% by weight of the D isomer of a cystine dialkyl ester and greater than about 75% by weight of the L isomer of a cystine dialkyl ester, less than about 10% by weight of the D isomer of a cystine dialkyl ester and greater than about 90% by weight of the L isomer of a cystine dialkyl ester, less than about 1% by weight of the D isomer of a cystine dialkyl ester and greater than about 99% by weight of the L isomer of a cystine dialkyl ester, greater than about 50% by weight of the D isomer of a cystine dialkyl ester and less than about 50% by weight of the L isomer of a cystine dialkyl ester, greater than about 75% by weight of the D isomer of a cystine dialkyl ester and less than about 25% by weight of the L isomer of a cystine dialkyl ester, greater than about 90% by weight of the D isomer of a cystine dialkyl ester and less than about 10% by weight of the L isomer of a cystine dialkyl ester, or greater than about 99% by weight of the D isomer of a cystine dialkyl ester and less than about 1% by weight of the L isomer of a cystine dialkyl ester.

In a still further embodiment, the cystine dialkyl ester can consist essentially of or consist of the D isomer of cystine dialkyl ester. In yet another embodiment, the cystine dialkyl ester can consist essentially of or consist of the L isomer of cystine dialkyl ester.

In some embodiments, the cystine dialkyl ester is a D-cystine dialkyl ester, or an adduct, a pharmaceutically acceptable salt, a tautomer, or a solvate thereof. Advantageously, it was found that D-isomer can be more active than the corresponding L-isomer of the cystine dialkyl ester and unlike L-cysteine does not increase upper airway resistance or promote cystinosis-like effects in animals or have negative cardiovascular effects of L-cysteine esters. The D-cystine dialkyl ester can be selected from the group consisting of D-cystine dimethyl ester, D-cystine diethyl ester, combinations thereof, or an adduct, a pharmaceutically acceptable salt, a tautomer, or a solvate thereof.

In some embodiments, the adduct of the cystine ester can be a biologically active adduct and include at least one of an albumin adduct, a glucose adduct, an L-cysteine adduct, an L-glutathione adduct, or an S-nitroso adduct.

Composition comprising a composition comprising a cystine ester described herein can be administered to a subject to attenuate opioid induced ventilatory and/or respiratory depression in the subject in need thereof. The opioid, which induces ventilatory and/or respiratory depression in the subject, can include, but is not limited to, alfentanil, buprenorphine, butorphanol, carfentanil, codeine, diamorphine, dextromoramide, dezocine, dihydrocodeine, fentanyl, hydrocodone, hydromorphone, levorphanol, meperidine, meptazinol, methadone, morphine, nalbuphine, nalorphine, opium, oxycodone, oxymorphone, pentazocine, propoxyphene, remifentanil, sufentanil, tapentadol, and tramadol, and pharmaceutically acceptable salts thereof. For example, the opioid can include morphine, carfentanil, fentanyl, remifentanil, or sufentanil.

In some embodiments, the opioid administration elicits disturbances in ventilatory parameters (e.g., decreases in frequency of breathing, tidal volume, and minute ventilation), Arterial Blood Gas (ABG) chemistry (e.g., decreases in pH, $pO_2$, $sO_2$ with increases in $pCO_2$) and Alveolar-arterial (A-a) gradient while causing sedation and analgesia.

In other embodiments, administration of the therapeutically effective amount of the composition is effective to elicit sustained reversal of opioid elicited disturbances in ventilatory parameters (e.g., decreases in frequency of breathing, tidal volume, and minute ventilation), Arterial Blood Gas (ABG) chemistry (e.g., decreases in pH, $pO_2$, $sO_2$ with increases in $pCO_2$) and Alveolar-arterial (A-a) gradient while augmenting opioid sedation and/or analgesia.

In some embodiments, the composition including the cystine ester can be administered to the subject to prevent the need for mechanical ventilation in subjects with acutely impaired ventilatory and/or respiratory drive because of an acute exacerbation of an underlying lung disease or an acute requirement for narcotic analgesia. For example, the subjects can be at-risk subjects with severe, hypercapneic COPD or mixed apnea evident on polysomnography.

In other embodiments, the subject can have or has an increased risk of cardio and/or respiratory depression that is caused, for example, by an anesthetic, a sedative, anxiolytic agent, a hypnotic agent, alcohol, and/or a narcotic. By way of a non-limiting example, narcotic analgesics (e.g., morphine, fentanyl, oxycodone, buprenorphine) are administered to cancer patients to alleviate pain. The dose is often limited by a fear of respiratory depression. In addition, even a partial respiratory depression from these drugs causes hypoxia and a resulting excessive daytime sleepiness that can be debilitating and severely decrease quality of life. General anesthetics can exert a similar depressant effect on respiration and delay a patient's transfer from the operating room to a surgical recovery area. A composition comprising a cystine ester described herein is therefore useful to counteract the lingering effects of the anesthetic, and for restoring adequate respiratory drive to enable the patient to breathe on their own.

In other embodiments, a composition including a cystine ester described herein can be administered in ambulatory delivery formulations to treat respiratory depression associated with narcotics, analgesics, sedatives, and/or opioids. The subject can be one who is taking and/or over-dosed on the narcotics, analgesics, sedatives, and/or opioids and who is experiencing or at risk of acute cardio and/or respiratory depression. The compositions can be administered to the subject to increase at least one of opioid depressed tidal volume, respiratory frequency, minute ventilation, mean arterial blood pressure, diastolic blood pressure, or systolic blood pressure.

In some embodiments, a subject can include a subject with an increased risk of decreased ventilatory and/or respiratory drive such as a subject with a significant chronic obstructive pulmonary disease, and those with a substantially decreased respiratory reserve, hypoxia, hypercapnia, or pre-existing respiratory depression. Elderly, cachectic, or debilitated subjects may have altered pharmacokinetics or altered opioid clearance compared to younger, healthier patients resulting in greater risk for respiratory depression.

In some embodiments, compositions including a cystine ester described herein can be administered to the subject in combination with at least one additional compound, agent, and/or therapeutic agent useful for treating the subject or the breathing disorder. These additional compounds, agents, and/or therapeutic agents can include commercially available agents or compounds, known to treat, prevent, or reduce the symptoms of breathing disorders or treat the disorder in the subject.

In some embodiments, the at least one additional therapeutic agent can change normal breathing in a subject. Such additional agents can be selected from the group consisting of an opioid, doxapram and enantiomers thereof, acetazolamide, almitrine, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In other embodiments, compositions comprising a cystine ester described herein and at least one additional compound has additive, complementary or synergistic effects in the treatment of the breathing disorder or other disorder in the subject. In a non-limiting example, the compositions that include a cystine ester described herein may be used concurrently or in combination with one or more of the following drugs: an opioid (e.g., morphine, oxycodone, fentanyl), doxapram, enantiomers of doxapram, acetazolamide, almitrine, theophylline, caffeine, methylprogesterone and related compounds, sedatives that decrease arousal threshold in sleep disordered breathing patients (e.g., eszopiclone and zolpidem), sodium oxybate, benzodiazepine receptor agonists (e.g., zolpidem, zaleplon, eszopiclone, estazolam, flurazepam, quazepam, temazepam, triazolam), orexin antagonists (e.g., suvorexant), tricyclic antidepressants (e.g., doxepin), serotonergic modulators, adenosine and adenosine receptor and nucleoside transporter modulators, cannabinoids (e.g., but not limited to, dronabinol), orexins, melatonin agonists (e.g., ramelteon) and compounds known as ampakines.

The combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the composition comprising a cystine ester described herein and an additional agent are physically mixed in the composition. In another embodiment, the composition comprising a cystine ester described herein and the additional agent are physically separated in the composition.

In one embodiment, compositions including a cystine ester described herein are co-administered with a compound that is used to treat another disorder but causes loss of breathing control. In this aspect, compositions including a cystine ester described herein block or otherwise reduce depressive effects on normal breathing control caused by the compound with which they are co-administered. An exemplary compound that treats another disorder but depresses breathing control includes but is not limited to anesthetics, sedatives, sleeping aids, anxiolytics, hypnotics, alcohol, and narcotic analgesics. The co-administered compound may be administered individually, or a combined composition as a mixture of solids and/or liquids in a solid, gel or liquid formulation or as a solution, according to methods known to those familiar with the art.

In some embodiments, a composition including a cystine ester described herein may be packaged with at least one additional compound useful for treating breathing control disorders. In another embodiment, a composition including a cystine ester described herein may be packaged with a therapeutic agent known to cause changes in breathing control, such as, but not limited to, anesthetics, sedatives, anxiolytics, hypnotics, alcohol, and narcotic analgesics. A co-package may be based upon, but not limited to, dosage units. For example, a composition can include an opioid capable of inducing cardio and/or respiratory depression in a subject and an amount of a cystine ester described herein effective to prevent the opioid induced cardio and/or respiratory depression when the composition is administered to the subject.

In some embodiments, an effective amount (i.e., dose) of a cystine ester described herein to be administered to a subject can be determined depending upon, for example, age, body weight, symptom, the desired therapeutic effect, the route of administration, and the duration of the treatment. Exemplary doses can be from about 0.01 to about 1000 mg, by oral administration. Examples of dose ranges can include from a minimum dose of about 0.01, 0.10, 0.50, 1, 5, 10, 25, 50, 100, 125, 150, 200, or 250 mg to a maximum dose of about 300, 400, 500, 600, 700, 800, 900, or 1000 mg, wherein the dose range can include from any one of the foregoing minimum doses to any one of the foregoing maximum doses. Specific examples of particular effective amounts contemplated via oral administration can include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 mg or more. The oral dose can be administered once daily, twice daily, three times daily, or more frequently.

The dose of the cystine ester for use in parenteral administration (e.g., intravenous administration) is generally from about 0.01 to about 300 mg/kg body weight. Examples of dose ranges can include from a minimum dose of about 0.01, 0.10, 0.50, 1, 5, 10, 25, 50, or 100 mg/kg body weight to a maximum dose of about 125, 150, 175, 200, 250, 275, or 300 mg/kg body weight, wherein the dose range can include from any one of the foregoing minimum doses to any one of the foregoing maximum doses. Specific examples of effective amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 mg/kg body weight or more. Continuous intravenous administration is also contemplated for from 1 to 24 hours per day to achieve a target concentration from about 0.01 mg/L blood to about 100 mg/L blood. Exemplary dose ranges can include from a minimum dose of about 0.01, 0.10, 0.25, 0.50, 1, 5, 10, or 25 mg/L blood to a maximum dose of about 40, 45, 50, 55, 60, 65, 70, 75, 80, 85, 90, or 100 mg/L, wherein an exemplary dose ranges can include from any one of the foregoing minimum doses to any one of the foregoing maximum doses. Specific examples of particular effective amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/L blood or more. The dose to be used can depend upon various conditions, and there may be cases wherein doses lower than or greater than the ranges specified above are used.

In some embodiments, the composition is administered concurrently with opioid administration and/or up to about 10 minutes, up to about 20 minutes, up to about 30 minutes, up to about 40 minutes, up to about 50 minutes, up to about 60 minutes, up to about 70 minutes, up to about 80 minutes, up to about 90 minutes, up to about 100 minutes, up to about 110 minutes, or up to about 120 minutes before or after initiation of opioid administration.

The cystine esters described herein may be administered in the form of, for example, solid compositions, liquid compositions, or other compositions for oral administration, injections, liniments, or suppositories for parenteral administration. Solid compositions for oral administration include compressed tablets, pills, capsules, dispersible powders, and granules. Capsules include hard capsules and soft capsules. In such solid compositions, the cystine ester can be admixed with an excipient (e.g., lactose, mannitol, glucose, microcrystalline cellulose, or starch), combining agents (e.g., hydroxypropyl cellulose, polyvinyl pyrrolidone, or magnesium metasilicate aluminate), disintegrating agents (e.g., cellulose calcium glycolate), lubricating agents (e.g., magnesium stearate), stabilizing agents, agents to assist dissolution (e.g., glutamic acid or aspartic acid), or the like. The agents may, if desired, be coated with coating agents (e.g., sugar, gelatin, hydroxypropyl cellulose, or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups, and elixirs. In such compositions, the cystine ester is dissolved, suspended, or emulsified in a commonly used diluent (e.g., purified water, ethanol, or mixture thereof). Furthermore, such liquid compositions may also comprise wetting agents, suspending agents, emulsifying agents, flavoring agents (e.g., flavor-masking agents) sweetening agents, perfuming agents, preserving agents, buffer agents, or the like.

Injections for parenteral administration include solutions, suspensions, emulsions, and solids, which are dissolved or suspended. For injections, the cystine ester can be dissolved, suspended, and/or emulsified in a solvent. The solvents are, for example, distilled water for injection, physiological salt solution, vegetable oil, propylene glycol, polyethylene glycol, alcohol such as ethanol, or a mixture thereof. Moreover the injections also can include stabilizing agents, agents to assist dissolution (e.g., glutamic acid, aspartic acid, or POLYSORBATE 80), suspending agents, emulsifying agents, soothing agents, buffer agents, preserving agents, etc. The compositions are sterilized in the final process or manufactured and prepared by sterile procedure. The compositions also can be manufactured in the form of sterile solid compositions, such as a freeze-dried composition, and can be sterilized or dissolved immediately before use in sterile distilled water for injection or some other solvent.

Other compositions for parenteral administration include liquids and ointments for external use, endermic liniments, compositions for inhalation, sprays, suppositories for rectal administration, and pessaries for vaginal administration, which compositions include a cystine ester and are administered by methods known in the art.

Compositions comprising a cystine ester described herein for inhalation or sprays may comprise additional substances other than diluents, such as, e.g., stabilizing agents (e.g., sodium sulfite hydride), isotonic buffers (e.g., sodium chloride, sodium citrate or citric acid). See, for example, the methods described in U.S. Pat. Nos. 2,868,691 and 3,095,355. The cystine ester can be effectively distributed by inhalation or spray using a self-propelling composition that includes a solution or dispersion of the cystine ester in micronized form. For example, an effective dispersion of finely divided drug particles can be accomplished with the use of very small quantities of a suspending agent, present as a coating on micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition can employ, as the suspending agent, a fatty alcohol such as oleyl alcohol. Propellants that may be employed include hydrofluoroalkane propellants and chlorofluorocarbon propellants. Dry powder inhalation also can be employed.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

Although the descriptions of pharmaceutical compositions provided herein are principally directed to pharmaceutical compositions, which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions is contemplated include, but are not limited to, humans and other primates, mammals including commercially relevant mammals such as cattle, pigs, horses, sheep, cats, and dogs.

The regimen of administration may affect what constitutes an effective amount. The therapeutic formulations may be administered to the patient either prior to or after the onset of a breathing disorder event or ventilator depressant effects of the opioid. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

Other embodiments described herein relate to a method of treating a subject in need thereof, such as a subject without normal ventilation and/or normal breathing control, by administering the compositions comprising a cystine ester described herein, and additionally treating the patient using a device to support breathing. Such devices include, but are not limited to, ventilation devices, CPAP and BiPAP devices.

Mechanical ventilation is a method to mechanically assist or replace spontaneous breathing. Mechanical ventilation is typically used after an invasive intubation, a procedure wherein an endotracheal or tracheostomy tube is inserted into the airway. It is normally used in acute settings, such as in the ICU, for a short period of time during a serious illness. It may also be used at home or in a nursing or rehabilitation institution, if patients have chronic illnesses that require long-term ventilation assistance. The main form of mechanical ventilation is positive pressure ventilation, which works by increasing the pressure in the patient's airway and thus forcing air into the lungs. Less common today are negative pressure ventilators (for example, the "iron lung") that create a negative pressure environment around the patient's chest, thus sucking air into the lungs. Types of mechanical ventilation are: conventional positive pressure ventilation, high frequency ventilation, non-invasive ventilation (non-invasive positive pressure ventilation or NIPPV), proportional assist ventilation (PAV), adaptive servo ventilation (ASV) and neurally adjusted ventilatory assist (NAVA).

Non-invasive ventilation refers to all modalities that assist ventilation without the use of an endotracheal tube. Non-invasive ventilation is primarily aimed at minimizing patient discomfort and the complications associated with invasive ventilation, and is often used in cardiac disease, exacerbations of chronic pulmonary disease, sleep apnea, and neuromuscular diseases. Non-invasive ventilation refers only to the patient interface and not the mode of ventilation used; modes may include spontaneous or control modes and may be either pressure or volume cycled modes.

Some commonly used modes of NIPPV include continuous positive airway pressure (CPAP). This kind of machine has been used mainly by patients for the treatment of sleep apnea at home, but now is in widespread use across intensive care units as a form of ventilatory support. The CPAP machine stops upper airway obstruction by delivering a stream of compressed air via a hose to a nasal pillow, nose mask or full-face mask, splinting the airway open (keeping it open under air pressure) so that unobstructed breathing becomes possible, reducing and/or preventing apneas and hypopneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

Bi-level positive airway pressure (BIPAP) alternate between inspiratory positive airway pressure (IPAP) and a lower expiratory positive airway pressure (EPAP), triggered by patient effort. On many such devices, backup rates may be set, which deliver IPAP pressures even if patients fail to initiate a breath.

The invention is further illustrated by the following example, which is not intended to limit the scope of the claims.

Example 1

We evaluated a novel class of thiol-based respiratory stimulants. The original compounds made use of the findings that erythrocytic hemoglobin transports not only $CO_2$ and 02, but also thiol-bound nitric oxide (NO), and that erythrocytic thiol-bound NO content decays logarithmically as a function of changes in oxyhemoglobin saturation. Thiol-containing compounds, such as glutathione or N-acetylcysteine (NAC) accelerate loss of NO from deoxyhemoglobin and can serve as potent respiratory stimulants, increasing minute ventilation in humans and animals. N-acetylcysteine signals erythrocytic hemoglobin desaturation and augments hypoxia-induced increases minute ventilation. Relative to placebo, humans receiving oral NAC three times daily had a three-fold greater increase in minute ventilation (24±4% versus 8±3%) when exposed acutely to isocapnic hypoxia. However, high NAC doses were required. We studied the details of this pathway worked out in both rat and transgenic mouse models.

To target this pathway, we screened thiol-containing compounds as respiratory stimulants. We discovered several that were more potent than NAC. Of these, the compounds with the most sustained activity were D-Cystine dimethylester (D-Cystine diME) and D-Cystine diethylester (D-Cystine diEE). We found that oxidized thiols, such as D-Cystine diME and D-Cystine diEE, may be longer-acting than the corresponding reduced thiols, such as D-Cysteine ethyl ester (D-CYSee), because they are more stable, with gradual reduction to the active, but shorter-acting, reduced form in vivo; this reduction has previously been demonstrated. The D-isomer may be more active than the corresponding L-isomer because of slower metabolism to intracellular cellular cysteine-containing peptides and proteins—permitting sustained activity. This was the starting premise, but our more recent work suggests additionally that D-Cystine diME may inhibit a specific potassium channel involved in respiratory control. We also found that modifications of the cysteine molecule, including simple N-acetylation, decrease activity.

These compounds can be used as a novel treatment option for COPD and other pulmonary patients with acute respiratory depression. The principal target population can include patients with impaired ventilatory and/or respiratory drive who are at risk for requiring mechanical ventilation because of either an acute exacerbation of underlying lung disease or an acute requirement for narcotic analgesia.

D-Cystine diME Given Parenterally Causes a Sustained Increase in Tidal Volume and Respiratory Frequency in Conscious Rats D-Cystine diME Increases Minute Ventilation in Conscious Rats Plethysmographic measurements in conscious male adult Sprague-Dawley rats revealed that D-Cystine diME (500 mol/kg, i.v.) elicited robust increases in frequency of breathing, tidal volume and minute ventilation of 20 min in duration (FIG. 1). Identical injections of D-CYSee (D-Cysteine ethyl ester) and L-CYSee (L-Cysteine ethyl ester) had similar effects, but D-Cystine diME provided the most sustained effect. We hypothesize that oxidized D-cystine esters have sustained activity because they are taken up into neuroregulatory cells and erythrocytes, slowly reduced to D-cysteine, but are not inactivated by incorporation into peptides and proteins by enzymes that recognize L-cysteine.

Figure 2I:
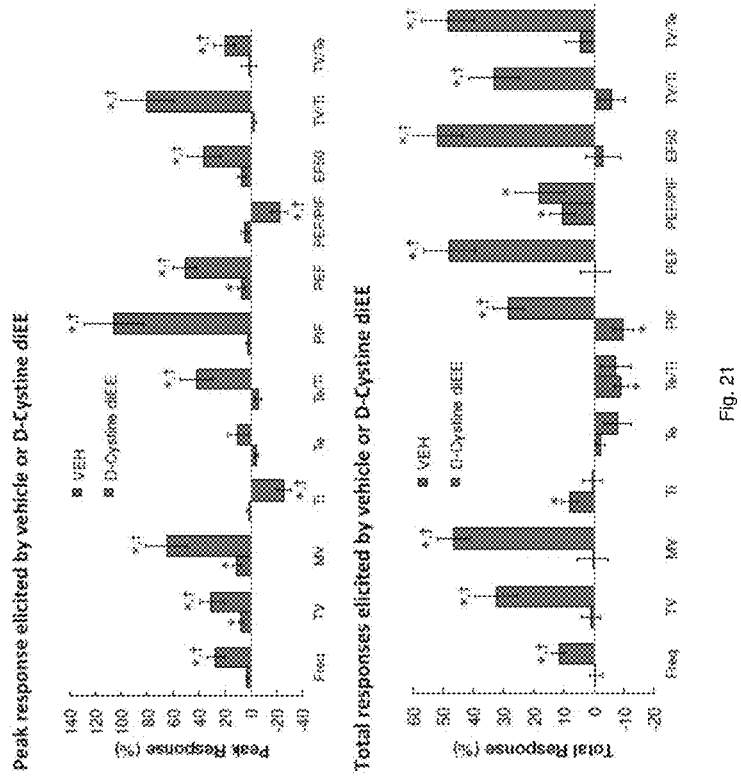
FIGS. 2(A-C) illustrate plots showing the total responses elicited by the test compounds (500 mol/kg, i.v.) in conscious rats. Each compound was given to a separate group of rats (n=8 rats per group). Data are mean±SEM. *P<0.05, significant response. †P<0.05, d-Cystine diME versus other agents.
Figure 6D:
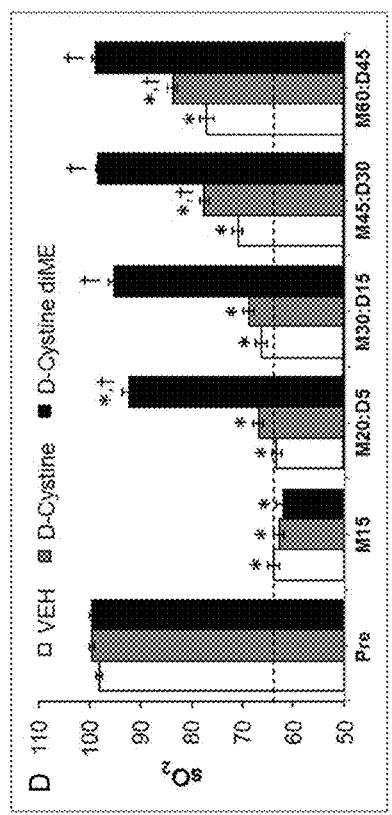
Figure 6E:
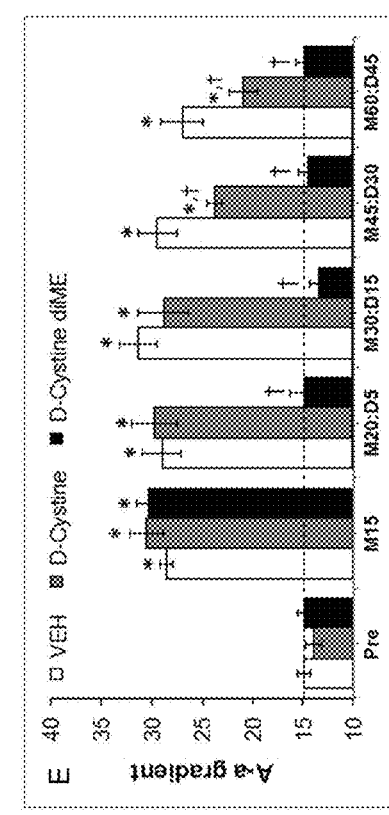

D-Cystine diME is the Most Active Member of this Novel Class of Respiratory Stimulants The total responses recorded over the 30 min post-injection period (% baseline) are summarized in FIG. 2. These data provide structure-activity relationship information. Injection of the vehicle (saline) elicited minor effects. L-serine ethyl ester (L-SERee), was minimally active, demonstrating the key importance of the sulfur atom in these responses. The comparatively minor effects of L-N-acetyl-cysteine methylester (L-NACme) demonstrate that placing acetyl moiety on the nitrogen atom of L-cysteine also impairs efficacy. Of key importance were the findings that (1) L-cysteine methylester (L-CYSme) was as efficacious as L-CYSee (L-Cysteine ethyl ester), (2) D-CYSee (D-Cysteine ethyl ester) was more efficacious that L-CYSee/L-CYSme, and (3) D-Cystine diME was the most efficacious of the test compounds.

Dose-Response Effects of D-Cystine diME in Conscious Rats

Figure 3B:
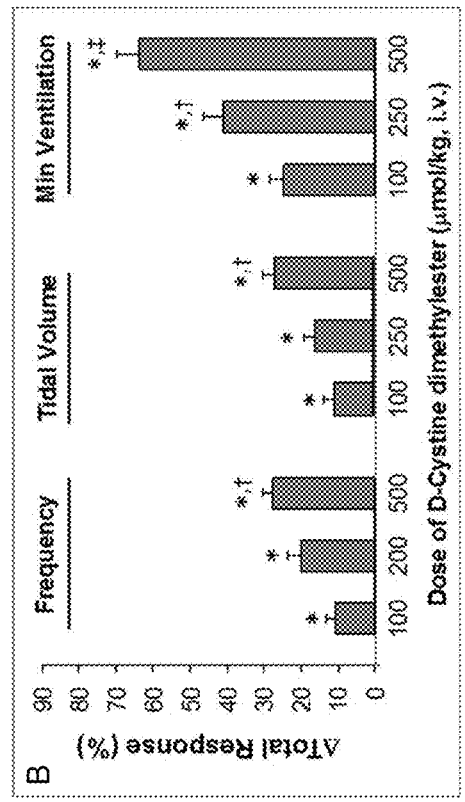

A key feature of therapeutic drug is dose-dependency. As shown in FIG. 3, the ventilatory responses elicited by D-CYS diME clearly dose-dependent.

D-Cystine diME Also Elicits Pronounced Ventilatory Responses in Conscious Mice

Figure 4A:
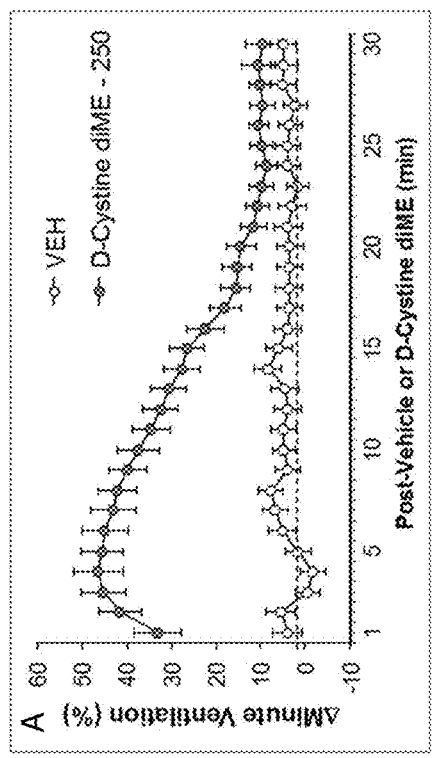
FIGS. 4(A-B) illustrate plots showing ventilatory responses elicited by vehicle (saline) or D-Cystine diME (250 μmol/kg, i.v.) in conscious mice. Each drug was given to a separate group of mice (n=8 mice per group). The data are presented as mean±SEM. *$P<0.05$, significant response. †$P<0.05$, d-CYS diME versus other agents.
Figure 4B:
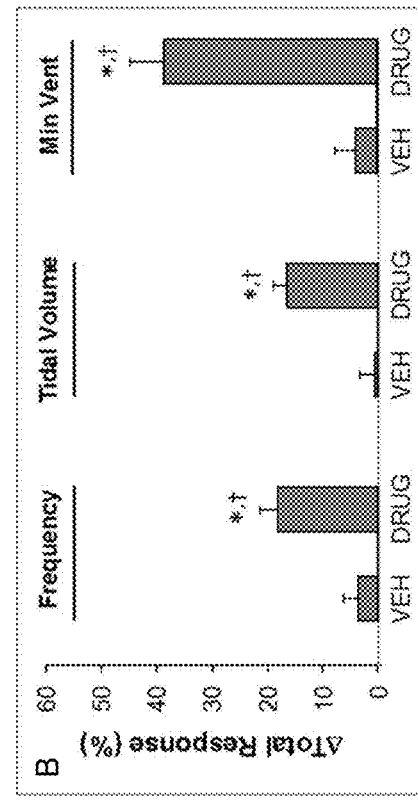

In order to assess whether the responses to D-Cystine diME were unique to rats, we examined the effects of a 250 mol/kg dose of D-Cystine diME on ventilatory parameters in conscious (adult male) C57 black 6 (C57BL6) mice. As seen in FIG. 4, this dose of D-Cystine diME elicited robust increases in frequency of breathing, tidal volume and minute ventilation of approximately 20 min in duration. The responses were equivalent to those in conscious rats.

Figure 5D:
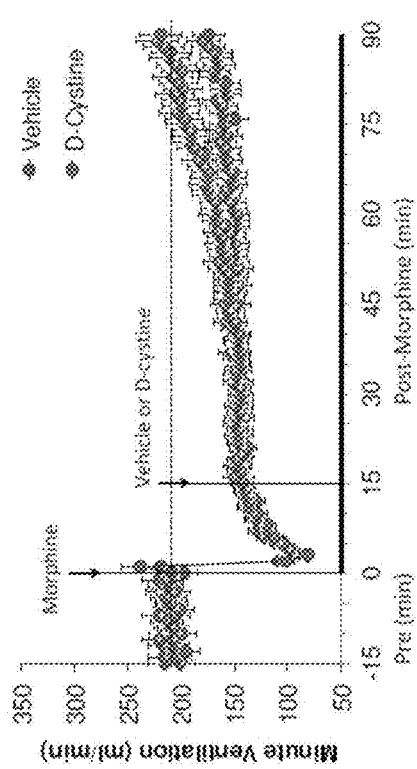
FIGS. 5(A-F) illustrate plots showing ventilatory responses including tidal volume/inspiratory time (Vt/Ti) elicited by vehicle (saline) or D-Cystine diEE (500 μmol/kg, i.v.) in rats which had received a bolus dose of morphine (10 mg/kg, i.v.). There were 9 rats in each group. Data are mean±SEM. *$P<0.05$, difference from pre-values. $^{†P<}0.05$, D-Cystine or D-Cystine diME versus vehicle.
Figure 5E:
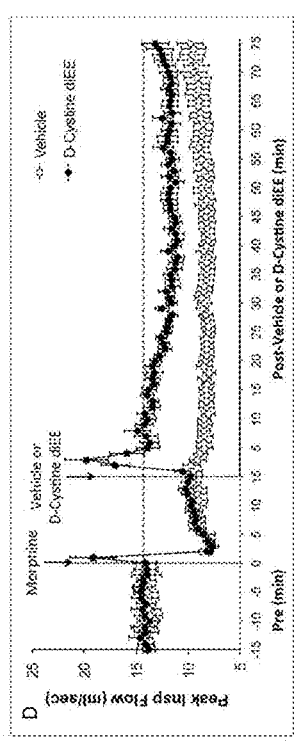
Figure 5F:
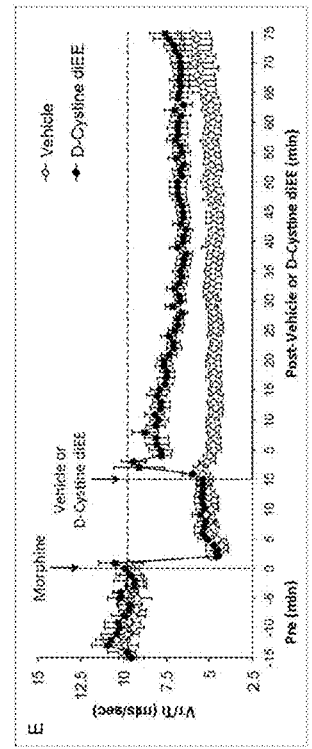
Figure 6A:
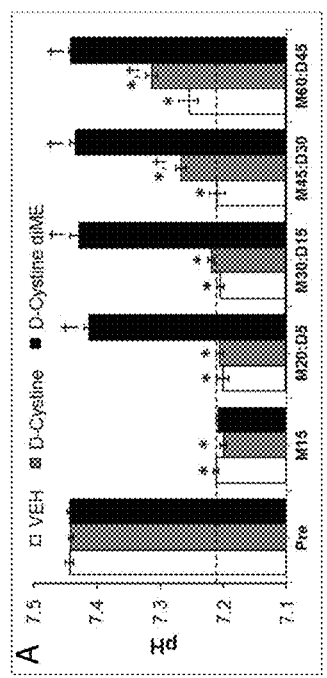
FIGS. 6(A-E) illustrate graphs showing the effects of D-Cystine (500 μmol/kg, i.v.) and D-Cystine diME (500 μmol/kg, i.v.) on arterial blood-gas chemistry and A-a gradients in rats which had previously received a bolus injection of morphine (10 mg/kg, i.v.). Data are mean±SEM (n=9 rats per group). *$P<0.05$, difference from pre-values. †$P<0.05$, D-Cystine or D-Cystine diME versus vehicle.
Figure 6B:
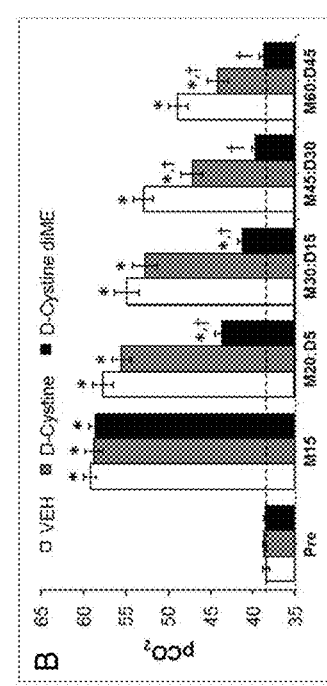
Figure 6C:
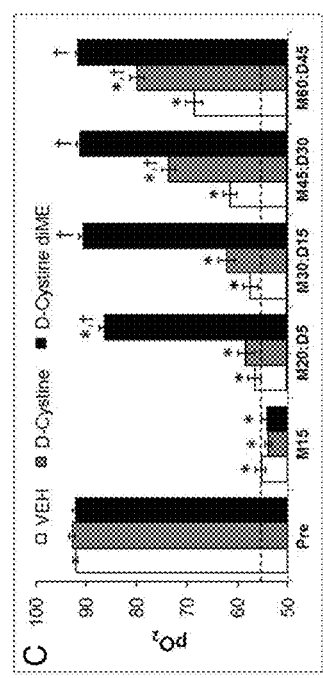
Figure 22:
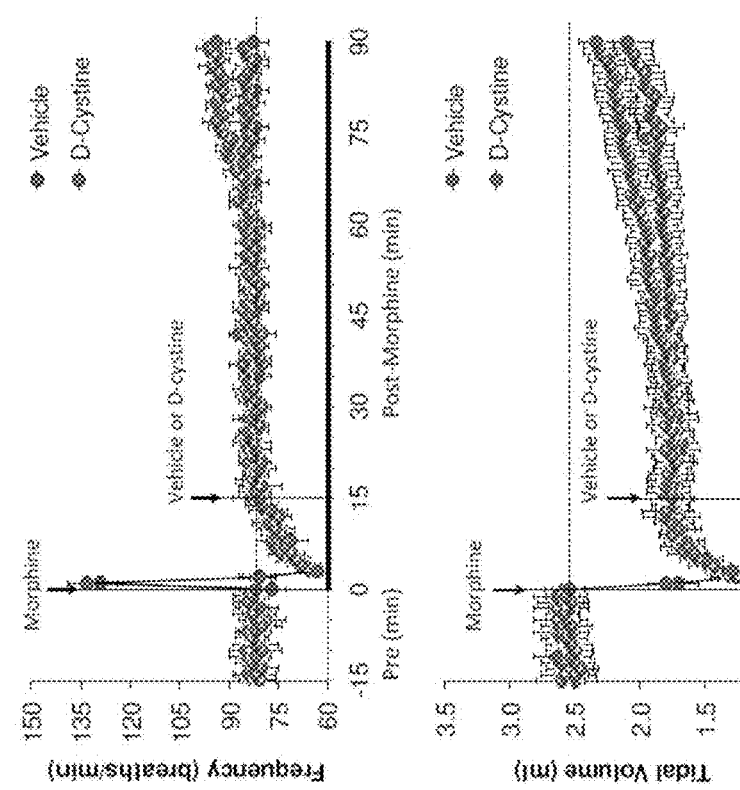

D-Cystine diEE and D-Cystine diME Reverse Opioid-Induced Respiratory Depression in Conscious Rats D-Cystine diEE Elicits an Immediate and Sustained Reversal of the Ventilatory Depressant Effects of Morphine As shown in FIG. 5, a bolus injection of D-Cystine diEE (500 µmol/kg, i.v.) elicited an immediate and sustained reversal of the ventilatory depressant effects of morphine (10 mg/kg, i.v.) including the derived parameter, tidal volume/inspiratory time (Vt/Ti), which is an index of central respiratory drive. The dramatic and sustained effect of D-Cystine diEE on tidal volume is a vital effect because the decrease in tidal volume is an integral component of morphine-induced changes in arterial blood-gas (ABG) chemistry (see below).

D-Cystine diME Reverses Morphine's Effects on ABG Chemistry

As shown in FIG. 6, the bolus injection of D-Cystine diME (500 µmol/kg, i.v.) reversed the deleterious actions of morphine (10 mg/kg, i.v.) on ABG chemistry and Alveolar-arterial (A-a) gradient (index of gas-exchange in the lungs). The bolus injection of D-cystine itself (500 µmol/kg, i.v.) elicited minor delayed effects (FIG. 6).

D-CYSee Reverses the Ventilatory Depressant Effects of Morphine

Figure 7A:
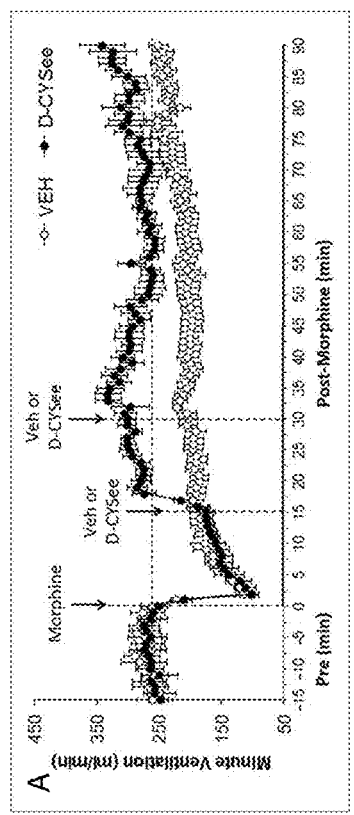
FIGS. 7(A-B) illustrate a plot and graph showing ventilatory responses including tidal volume/inspiratory time (Vt/Ti) elicited by vehicle (saline) or D-CYSee (2×500 μmol/kg, i.v.) in rats which had received a bolus dose of morphine (10 mg/kg, i.v.). There were 9 rats in each group. Data are mean±SEM. *$P<0.05$, difference from pre-values. †$P<0.05$, D-Cystine diME versus vehicle.
Figure 7B:
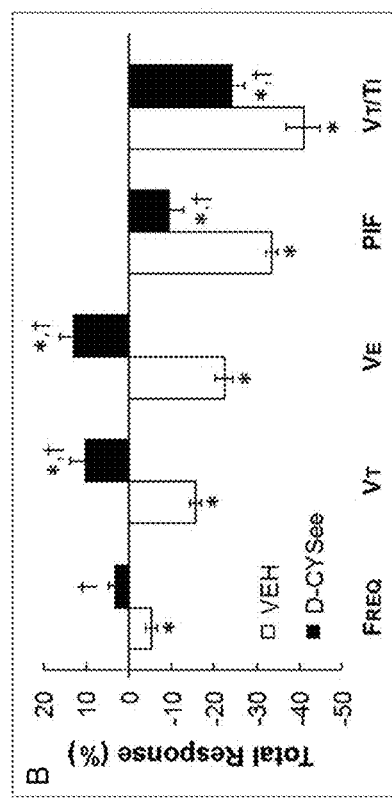

As shown in FIG. 7, the possibility that D-cystine diME exerts its effects via generation of D-Cysteine in cells is supported by findings that injections of D-CYSee (2×500 µmol/kg, i.v.) also elicited a sustained reversal of the effects of morphine (10 mg/kg, i.v.). As with D-Cystine diME, a key feature of D-CYSee is its ability to reverse the effects of morphine on tidal volume.

D-CYSee Reverses Morphine's Effects on ABG Chemistry and A-a Gradient

As seen in FIG. 8, a single injection of D-CYSee (500 µmol/kg, i.v.) elicited a sustained reversal of the deleterious effects of morphine (10 mg/kg, i.v.) on ABG chemistry and A-a gradient. D-cysteine itself (500 µmol/kg, i.v.) elicited minimal effects.

Prior Infusion of L-CYSee Blunts the Ventilatory Depressant Effects of Morphine

Figure 9D:
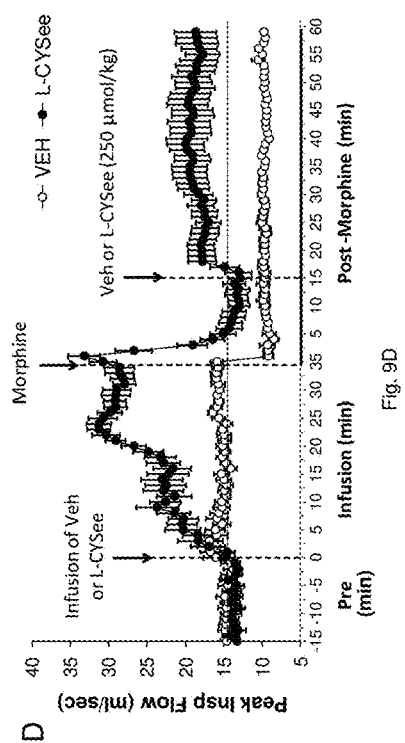
FIGS. 9(A-E) illustrate plots showing the effects of prior infusion of L-CYSee (total dose of 500 μmol/kg, i.v.) on the ventilatory depressant effects of morphine (10 mg/kg, i.v.) in conscious rats. Responses elicited by a bolus injection of L-CYSee (250 μmol/kg, i.v.) are also shown. Data are presented mean±SEM (n=9 rats per group).
Figure 9E:
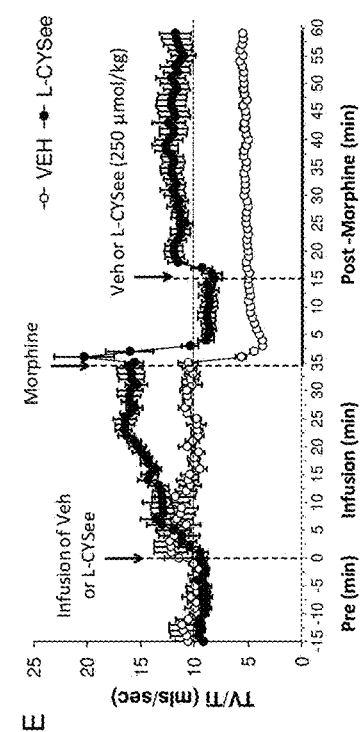

Although the ability of bolus injections of D-Cystine diME and D-CYSee to reverse opioid-induced depression of ventilation is of vital importance, it is also important to determine whether prior administration of these compounds can prevent the deleterious actions of opioids. Although we are yet to examine the D-isomers, we have established that prior infusion of L-CYSee (14.3 µmol/kg/min, total dose of 500 µmol/kg, i.v.) over 35 min (1) dramatically increased peak inspiratory flow and respiratory drive (Vt/Ti) in conscious rats, and (2) markedly blunted the subsequent effects of a bolus injection of morphine (10 mg/kg, i.v.). As can be seen, a subsequent injection of L-CYSee (250 µmol/kg/min) elicited prompt beneficial effects in these rats (FIG. 9).

Prior Infusion of L-CYSee but not L-SERee Blunts Morphine's Effects on ABG Chemistry and A-a Gradient As seen in FIG. 10, the prior infusion of L-CYSee 14.3 µmol/kg/min, total dose of 500 µmol/kg, i.v. over 35 min) virtually eliminated the deleterious effects of morphine (10 mg/kg, i.v.) on ABG chemistry and A-a gradient. In contrast, the infusion of identical amount of L-SERee was without effect on morphine, again high-lighting the key involvement of the sulfur atom in the beneficial effects of L-CYSee.

Preliminary Toxicology Studies

Hemodynamics

Figure 11A:
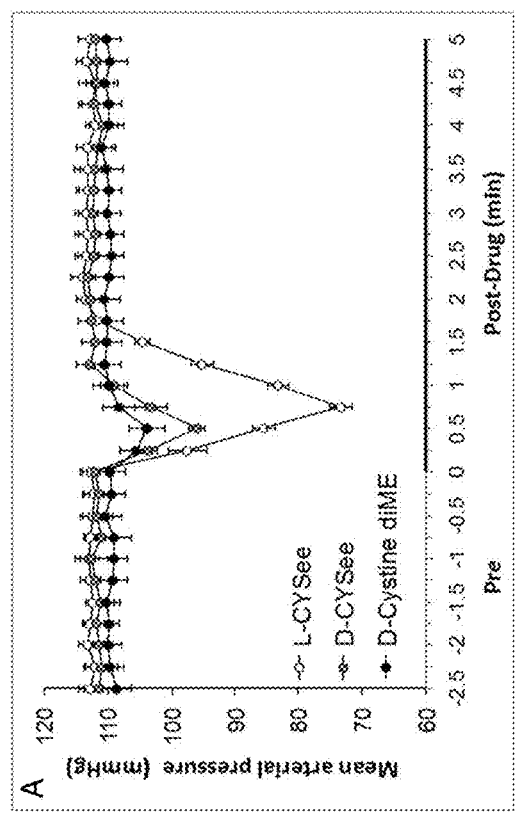
FIGS. 11(A-C) illustrate plots showing the effects of test agents (500 μmol/kg, i.v.) on hemodynamic variables. Data are presented mean±SEM (n=8 rats per group). D-Cystine diME did not elicit significant responses ($P>0.05$ for all comparisons to Pre).
Figure 11B:
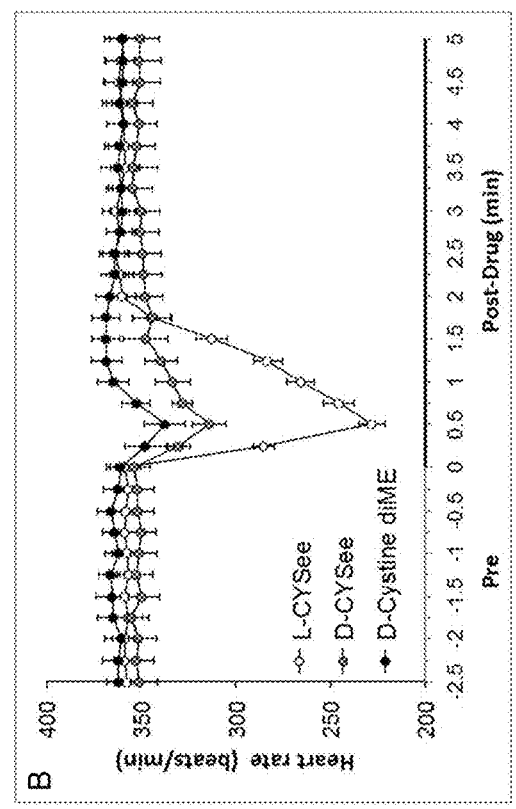
Figure 11C:
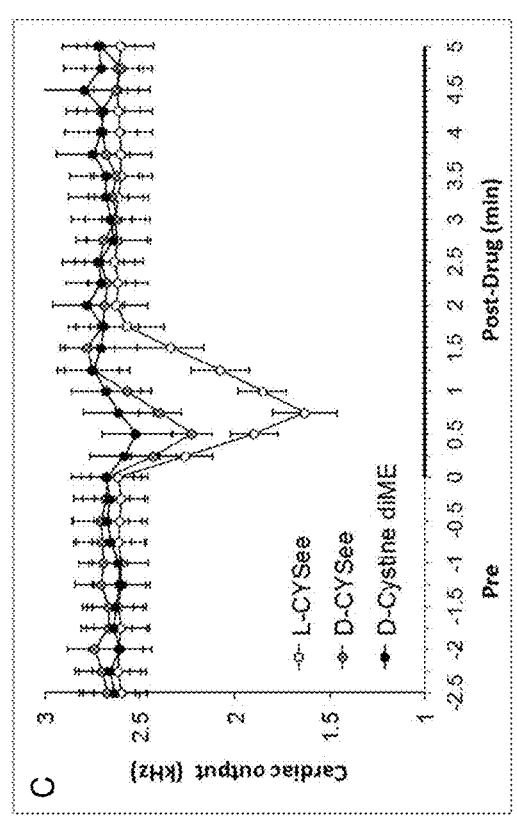

L-CYSee (500 µmol/kg, i.v.) elicited substantial transient decreases in mean arterial blood pressure (MAP) via decreases in cardiac output and heart rate (no changes in total peripheral resistance). In contrast, L-CYSee, and in particular D-Cystine diME, elicited minimal responses (FIG. 11).

Analgesia

Figure 12:
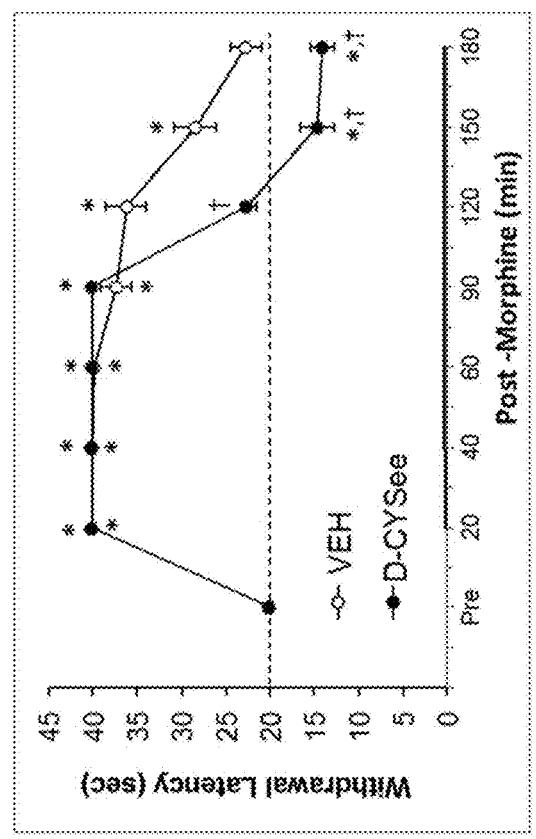
FIG. 12 illustrates a plot showing the effects of pretreatment with D-CYSee (500 μmol/kg, i.v.) on morphine-induced (5 mg/kg, i.v.) analgesia (paw withdrawal latency assay) in conscious rats. The data are presented as mean±SEM (n=6 rats per group). *$P<0.05$, difference from pre-values. †$P<0.05$, D-CYSee versus vehicle.
Figure 13:
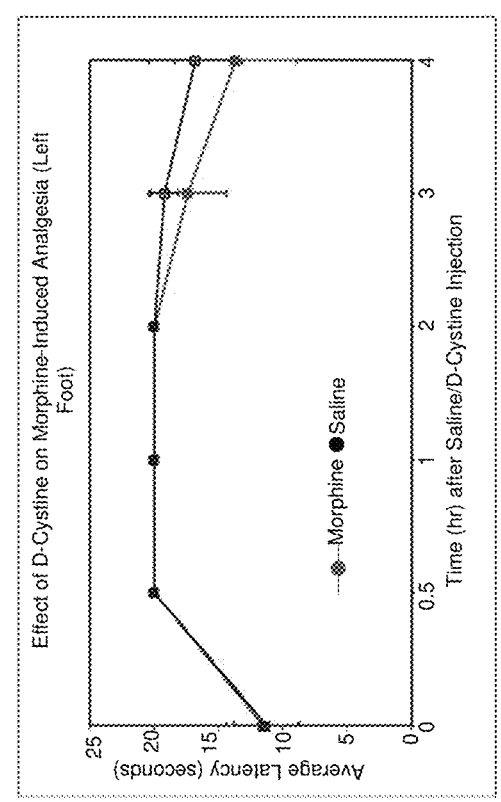
FIG. 13 illustrates a plot showing the effects of D-cystine diME on morphine induced analgesia.

Although pretreatment with D-CYSee (500 µmol/kg, i.v.) did not affect the initial level of analgesia (paw withdrawal latency) elicited by morphine (5 mg/kg, i.v.) in conscious rats, the analgesia decayed more quickly (FIG. 12). D-cystine diethyl ester (D-cystine DEE) (500 µmol/kg, i.v.) however does not attenuate morphine analgesia elicited by 10 mg/kg of morphine (dose eliciting depression of breathing in our ventilatory studies) (FIG. 13), suggesting it may be an ideal respiratory stimulant in the setting of narcotic-induced respiratory depression.

Example 2

This example describes the effects of d-cystine ethyl ester (d-cystine diEE) and d-cystine methyl ester (d-cystine diME) on the actions of morphine in freely moving adult male Sprague-Dawley rats. We found that systemic injection of d-cystine diEE or d-cystine diME elicits a rapid and sustained reversal of the negative effects of morphine on ventilatory parameters, A-a gradient and ABG chemistry whereas it augmented the analgesic actions of the opioid agonist. This pharmacological profile would be advantageous in many clinical settings involving patients who require opioids for essential pain relief (e.g., those just having undergone surgery) and who cannot be administered opioid receptor antagonists to overcome serious ventilatory depression.

Methods

Permissions, rats, surgical procedures and blinding of protocols. All studies were carried out in accordance with the NIH Guide for the Care and Use of Laboratory Animals (NIH Publication No. 80-23) revised in 1996. The protocols were approved by the Animal Care and Use Committees of the University of Virginia, Case Western Reserve University and Loma Linda University. In addition, all studies were carried out in compliance with the ARRIVE (Animal Research: Reporting of In Vivo Experiments) guidelines. Adult male Sprague-Dawley rats (Harlan, Madison, WI, USA) were implanted with jugular vein catheters under 2% isoflurane anesthesia and some rats received femoral arterial catheters. The rats were allowed at least four days to recover from surgery before use. All arterial catheters were flushed daily with heparin solution (50 units of heparin in phosphate-buffered saline at 0.1 M, pH 7.4). All catheters were flushed with phosphate-buffered saline (0.1 M, pH 7.4) approximately four hours before commencement of the experiments. All studies were performed in a quiet laboratory with relative humidity of 49±2% and room temperature of 21.4±0.2° C. Please note that in the studies described in the main manuscript below, we examined the effects d-cystine diEE against morphine in the plethysmography studies and the effects of d-cystine diME in the arterial blood gas/A-gradient and antinociception studies. Also, please note that the antinociception and ventilatory studies were done in separate groups of rats so as to not complicate the respiratory measurements. The recording (plethysmography, antinociception) sessions and the arterial blood gas assays were done by a particular investigator who administered the opioid, vehicle or test drug such as d-cystine diME. The syringes containing the vehicle or test drug were made up by another investigator, such that the investigator running the actual experiment was blinded to the treatment protocol. In every case, the data files resulting from a particular study were first collated and analyzed by another investigator in the group.

Whole-Body Plethysmography Measurement of Ventilatory Parameters

Ventilatory parameters were recorded in freely moving rats by whole body plethysmography (PLY3223; Data Sciences International, St. Paul, MN). The rats were placed in individual chambers and given 60 min to acclimatize to allow true resting ventilatory parameters to be established. Two groups of rats received a bolus injection of morphine (10 mg/kg, IV) and after 15 min, one group received an injection of vehicle (saline) whereas the other received an injection of d-cystine diEE (500 μmol/kg, IV) and ventilatory parameters were recorded for a further 75 min. Two groups of rats received a bolus injection of morphine (10 mg/kg, IV) and after 15 min, one group received an injection of vehicle (saline) whereas the other received an injection of d-cystine (500 μmol/kg, IV) and ventilatory parameters were recorded for a further 75 min. We thought it appropriate to also determine whether the thiolester, 1-N-acetylcysteine methyl ester (1-NACme), which is a highly cell penetrable reducing agent, would reverse the negative effects of morphine on breathing. Two groups of rats received a bolus injection of morphine (10 mg/kg, IV) and after 15 min, one group received an injection of vehicle (saline) whereas the other received an injection 1-NACme (500 μmol/kg, IV). The rats received another injection of vehicle or 1-NACme (500 μmol/kg, IV) 15 min later and ventilatory parameters were recorded for a further 60 min.

TABLE 1

Baseline (pre) values in the groups of rats that would receive vehicle of D-cystine diEE

| Parameter | Vehicle | D-Cystine diEE |
|---|---|---|
| Age, days | 78.3 ± 0.4 | 78.0 ± 0.6 |
| Body weights, gram | 338 ± 2 | 337 ± 2 |
| Frequency, breaths/min | 79.5 ± 4.5 | 83.7 ± 5.4 |
| Tidal Volume (TV), ml | 2.53 ± 0.17 | 2.44 ± 0.13 |
| Minute Ventilation, ml/min | 198 ± 14 | 200 ± 12 |
| Inspiratory Time (Ti), sec | 0.261 ± 0.012 | 0.240 ± 0.010 |
| Expiratory Time (Te), sec | 0.503 ± 0.032 | 0.476 ± 0.051 |
| Inspiratory Time/Expiratory Time | 1.93 ± 0.12 | 2.03 ± 0.25 |
| Peak Inspiratory Flow, ml/sec | 14.1 ± 0.9 | 14.2 ± 0.8 |
| Peak Expiratory Flow, ml/sec | 10.1 ± 0.7 | 10.5 ± 0.3 |
| Peak Expiratory Flow/Peak Inspiratory Flow | 0.73 ± 0.03 | 0.77 ± 0.06 |
| $EF_{50}$, ml/sec | 0.34 ± 0.02 | 0.37 ± 0.02 |
| Inspiratory Drive (TV/Ti), ml/sec | 9.7 ± .7 | 10.3 ± 0.3 |
| Inspiratory Drive (TV/Te), ml/sec | 5.2 ± 0.4 | 5.5 ± 0.5 |

D-Cystine diEE, D-cystine diethyl ester. The data are presented as mean ± SEM. There were 9 rats in each group. There were no between group differences for any parameter (P > 0.05, for all comparisons).

TABLE 2

Morphine-induced ventilatory responses in rats that subsequently received vehicle or D-Cystine diEE

| | Peak Responses (% change) | | Total Response (% change) | |
|---|---|---|---|---|
| Parameters | Vehicle | D-Cystine diEE | Vehicle | D-Cystine diEE |
| Frequency, breaths/min | −21.5 ± 3.4* | −20.0 ± 4.5* | +0.3 ± 4.3 | −1.9 ± 6.6 |
| Tidal Volume (TV), ml | −42.9 ± 8.7* | −35.8 ± 6.9* | −29.3 ± 7.6* | −26.3 ± 7.4* |

TABLE 2-continued

Morphine-induced ventilatory responses in rats that subsequently received vehicle or D-Cystine diEE

| Parameters | Peak Responses (% change) | | Total Response (% change) | |
|---|---|---|---|---|
| | Vehicle | D-Cystine diEE | Vehicle | D-Cystine diEE |
| Minute Ventilation, ml/min | −51.2 ± 6.3* | −48.5 ± 6.0* | −28.6 ± 7.2* | −28.4 ± 6.4* |
| Inspiratory Time (Ti), sec | +37.9 ± 3.0* | +41.3 ± 7.1* | +38.6 ± 2.9* | +40.2 ± 6.3* |
| Expiratory Time (Te), sec | −29.3 ± 17.1 | −32.4 ± 17.6 | −4.7 ± 6.0 | −2.0 ± 6.1 |
| Inspiratory Time/ Expiratory Time | −38.0 ± 4.2* | −41.7 ± 7.8* | −24.1 ± 4.7* | −27.1 ± 6.2* |
| Peak Inspiratory Flow, ml/sec | −45.6 ± 7.0* | −43.2 ± 2.7* | −29.5 ± 8.1* | −29.7 ± 2.7* |
| Peak Expiratory Flow, ml/sec | −38.1 ± 8.5* | −34.8 ± 6.7* | −17.4 ± 6.1* | −16.2 ± 5.7* |
| Peak Expiratory Flow/Peak Inspiratory Flow | +30.2 ± 3.4* | +26.7 ± 5.4* | +27.6 ± 7.0* | +21.5 ± 6.7* |
| $EF_{50}$, ml/sec | +133 ± 42* | +122 ± 27* | +30.5 ± 14.7* | +33.4 ± 15.0* |
| Inspiratory Drive (TV/Ti), ml/sec | −52.7 ± 5.4* | −53.7 ± 6.0* | −44.3 ± 7.1* | −44.5 ± 5.5* |
| Expiratory Drive (TV/Te), ml/sec | −51.5 ± 10.1* | −46.2 ± 7.8* | −22.3 ± 13.6 | −14.6 ± 10.2 |

D-Cystine diEE, D-cystine diethyl ester (500 μmol/kg, IV). The data are presented as mean ± SEM. There were 9 rats in each group. There were no between group differences for any parameter (P > 0.05, for all comparisons).
*P < 0.05, D-Cystine diEE versus vehicle.

TABLE 3

Morphine-induced responses in rats that subsequently received vehicle or D-Cystine

| Parameters | Stage of Experiment | Treatment Groups | |
|---|---|---|---|
| | | Vehicle | D-Cystine |
| Number | Morning of experiment | 9 | 9 |
| Age, days | Morning of experiment | 79.7 ± 0.4 | 80.0 ± 0.5 |
| Body weights, g | Morning of experiment | 340 ± 2 | 341 ± 3 |
| Frequency | Pre values | 82 ± 5 | 81 ± 6 |
| | Morphine - peak (+) response (%) | +57 ± 8* | +62 ± 7* |
| | Morphine peak (−) response (%) | −21 ± 3* | −23 ± 4* |
| | Morphine - first 15 min response (%) | −3.8 ± 2.6 | −4.7 ± 3.1 |
| | Drug maximum, % change | −2.4 ± 1.3 | −1.2 ± 2.1 |
| | Drug - entire 75 min, % change | +1.7 ± 0.9 | +4.5 ± 3.3 |
| | Drug - last 15 min, % change | +2.0 ± 0.9* | +14.3 ± 2.8*,† |
| Tidal Volume | Pre values | 2.59 ± 0.15 | 2.52 ± 0.14 |
| | Morphine - peak (+) response (%) | −32 ± 5* | −30 ± 4* |
| | Morphine peak (−) response (%) | −49 ± 5* | −51 ± 6* |
| | Morphine - first 15 min response (%) | −37 ± 6* | −35 ± 5* |
| | Drug maximum, % change | +1.8 ± 0.9 | +3.4 ± 2.2 |
| | Drug - entire 75 min, % change | −30 ± 5* | −22 ± 4* |
| | Drug - last 15 min, % change | −24 ± 4* | −12 ± 2*,† |

TABLE 3-continued

Morphine-induced responses in rats that subsequently received vehicle or D-Cystine

| Parameters | Stage of Experiment | Treatment Groups | |
|---|---|---|---|
| | | Vehicle | D-Cystine |
| Minute Ventilation | Pre values | 214 ± 15 | 207 ± 14 |
| | Morphine - peak (+) response (%) | +9 ± 3* | +14 ± 3* |
| | Morphine peak (−) response (%) | −60 ± 9* | −61 ± 8* |
| | Morphine - first 15 min response (%) | −39 ± 4* | −38 ± 5* |
| | Drug maximum, % change | −0.7 ± 1.3 | −4.4 ± 2.5 |
| | Drug - entire 75 min, % change | −29 ± 4* | −19 ± 5* |
| | Drug - last 15 min, % change | −23 ± 4* | −2 ± 4*,† |

Drug refers to an injection of vehicle or D-cystine (500 μmol/kg, IV). The data are presented as mean ± SEM. There were 9 rats in each group. There were no between group differences for any Pre-value ($P > 0.05$, for all comparisons.
*$P < 0.05$, significant response.
†$P < 0.05$, value in the D-cystine group versus value in the vehicle group.

TABLE 4

Ventilatory responses elicited by morphine and subsequent injections of vehicle or N-acetyl-L-cysteine dimethyl ester (L-NACme)

| Parameters | Stage of Experiment | Treatment Groups | |
|---|---|---|---|
| | | Vehicle | L-NACme |
| Number | Morning of experiment | 9 | 9 |
| Age, days | Morning of experiment | 80.0 ± 0.5 | 79.7 ± 0.4 |
| Body weights, g | Morning of experiment | 337 ± 3 | 336 ± 2 |
| Frequency | Pre values | 99 ± 3 | 98 ± 4 |
| | Morphine - peak (+) response (%) | +47 ± 6* | +42 ± 6* |
| | Morphine peak (−) response (%) | −24 ± 3* | −22 ± 4* |
| | Morphine - first 15 min response (%) | −4.0 ± 2.1 | −4.9 ± 2.8 |
| | Drug - entire 75 min, % change | +18 ± 4* | +11 ± 2* |
| Tidal Volume | Pre values | 2.62 ± 0.13 | 2.61 ± 0.16 |
| | Morphine - peak (+) response (%) | −19 ± 3* | −16 ± 6* |
| | Morphine peak (−) response (%) | −38 ± 5* | −40 ± 6* |
| | Morphine - first 15 min response (%) | −33 ± 4* | −34 ± 3* |
| | Drug - entire 75 min, % change | −23 ± 4* | −22 ± 3* |
| Minute Ventilation | Pre values | 256 ± 6 | 259 ± 17 |
| | Morphine - peak (+) response (%) | +19 ± 5* | +20 ± 6* |
| | Morphine peak (−) response (%) | −53 ± 5* | −54 ± 4* |
| | Morphine - first 15 min response (%) | −36 ± 3* | −35 ± 3* |
| | Drug - entire 75 min, % change | −15 ± 2* | −19 ± 4* |

Drug refers to two injections of vehicle or N-acetyl-L-cysteine ethyl ester (L-NACme; 500 μmol/kg, IV). The data are presented as mean ± SEM. There were 9 rats in each group. There were no between group differences for any Pre-value ($P > 0.05$, for all comparisons.
*$P < 0.05$, significant response.
†$P < 0.05$, value in the D-cystine group versus value in the vehicle group.

TABLE 5

Tail-Flick latency values elicited by morphine and subsequent injections of vehicle or D-Cystine

| Phase | Time (min) | Tail-Flick latency (sec) | |
|---|---|---|---|
| | | Vehicle | D-Cystine |
| Pre | −20 | 2.8 ± 0.3 | 2.9 ± 0.3 |
| 10 min-post drug | −10 | 2.9 ± 0.3 | 3.3 ± 0.4 |
| 20 min post-drug | 0 | 2.9 ± 0.2 | 3.2 ± 0.4 |
| post-morphine - 30 min | 30 | 12 ± 0.0* | 12 ± 0.0 |
| post-morphine - 60 min | 60 | 12 ± 0.0* | 12 ± 0.0 |
| post-morphine - 90 min | 90 | 11.7 ± 0.2* | 12 ± 0.0 |
| post-morphine - 120 min | 120 | 11.1 ± 0.2* | 12 ± 0.0*,† |
| post-morphine - 180 min | 180 | 8.3 ± 0.3* | 10.7 ± 0.3*,† |
| post-morphine - 210 min | 210 | 5.6 ± 0.3* | 7.4 ± 0.3*,† |
| post-morphine - 240 min | 240 | 4.3 ± 0.3* | 5.0 ± 0.3* |
| post-morphine - 360 min | 360 | 3.3 ± 0.3 | 3.5 ± 0.3 |

The dose of D-cystine was 500 μmol/kg, IV. The data are presented as mean ± SEM. There were 9 rats in each group. There were no between group differences for any Pre-value and neither vehicle or D-cystine elicited immediate effects as measured 10 and 20 min post-injection ($P > 0.05$, for all comparisons.
*$P < 0.05$, significant difference from Pre-values.
†$P < 0.05$, D-cystine versus vehicle.

Due to the closeness of the body weights of all of the groups of rats, ventilatory data are shown without any corrections for body weight. The provided software (Fine Pointe, BUXCO) constantly corrected digitized values for changes in chamber temperature and humidity. Pressure changes associated with the respiratory waveforms were then converted to volumes (i.e., TV, PIF and PEF) using the algorithm of Epstein and colleagues. Specifically, factoring in chamber temperature and humidity, the cycle analyzers filtered the acquired signals, and BUXCO algorithms (Fine Pointe) generated an array of box flow data that identified a waveform segment as an acceptable breath. From that data vector, the minimum and maximum values were determined. Flows at this point were considered to be "box flow" signals. From this array, the minimum and maximum box flow values were determined and multiplied by a compensation factor provided by the selected algorithm, thus producing TV, PIF and PEF values that were used to determine accepted and rejected waveforms, with rejected waveforms remaining below 5% throughout all phases of the protocols except for a transient rise in rejection of breaths to 15-20% for 1-2 min after injection of morphine (data not shown).

Protocols for Blood Gas Measurements and Determination of Arterial-Alveolar Gradient.

The changes in pH, $pCO_2$, $pO_2$ and $sO_2$ elicited by injection of morphine (10 mg/kg, IV) in 3 separate groups of freely moving rats (n=9 rats per group) followed 15 min later by injection of vehicle (saline; 80.0±0.6 days of age; 342±2 g body weight), d-cystine (500 µmol/kg, IV; 79.7±0.4 days; 340±2 g) or d-cystine diME (500 µmol/kg, IV; 79.3±0.4 days; 338±2 g) were determined. Arterial blood samples (100 µL) were taken 15 min before and 15 min after injection of morphine (10 mg/kg, IV). The rats then immediately received an injection of vehicle, d-cystine or d-cystine diME and blood samples were taken 5, 15, 30 and 45 min later. The pH, $pCO_2$, $pO_2$ and $sO_2$ were measured using a Radiometer blood-gas analyzer (ABL800 FLEX). The A-a gradient measures difference between alveolar and arterial blood $O_2$ concentrations. A decrease in $PaO_2$, without a change in A-a gradient is normally accompanied by an increase in $paCO_2$ (as observed here) if it is caused by hypoventilation. Hypoxia is irreversible if caused by shunt. An increased A-a gradient is caused either by oxygen diffusion limitation (usually not readily reversible) or ventilation-perfusion mismatch. A-a gradient=$PAO_2$—$PaO_2$, where $PAO_2$ is the partial pressure of alveolar $O_2$ and $PaO_2$ is $pO_2$ in arterial blood. $PAO_2=[(FiO_2\times(P_{atm}-P_{H2O})(PaCO_2/\text{respiratory quotient})]$, where $FiO_2$ is the fraction of $O_2$ in inspired air; $P_{atm}$ is atmospheric pressure; $P_{H2O}$ is the partial pressure of $H_2O$ in inspired air; $PaCO_2$ is $pCO_2$ in arterial blood; and respiratory quotient (RQ) is the ratio of $CO_2$ eliminated/$O_2$ consumed. We took $FiO_2$ of room-air to be 21%=0.21, $P_{atm}$ to be 760 mmHg, and $P_{H2O}$ to be 47 mmHg23. We did not determine RQ values directly, but took the resting RQ value of our adult male rats to be 0.9 on the basis of work by others. We used a RQ value of 0.9 to calculate A-a gradient throughout the blood-gas protocols on the assumption that morphine and the thiolesters do not directly affect this value, although this must be directly addressed in our protocols at some point. Here, we had both alveolar hypoventilation and ventilation-mismatch. In almost all cases, when these two phenomena occur together and are readily reversed, the cause is decreased minute ventilation leading rapidly to atelectasis.

Antinociception Protocols
Tail-Flick Latency (TFL)

The antinociceptive effects of morphine, vehicle and d-cystine diEE were assessed by tail-flick latency (TFL) test using a Tail-Flick Analgesia Meter (IITC Life Science Inc., USA). This involved minor manual restraint while positioning the tail to apply a thermal stimulus sufficient to induce a latency of tail withdrawal of about 3.0 s in all animals. Baseline TFL was tested in all rats (−20 min time-point in FIG. 32). One group of rats (79.0±0.6 days of age; 338±2 g body weight, n=9 rats) received an IV injection of vehicle (saline, 100 µL/100 g body weight) and the second group (79.7±0.6 days; 342±2 g, n=9 rats) received an injection of d-cystine diEE (500 µmol/kg, IV). TFL was tested in both groups 10 and 20 min later (— 10 and 0 min in FIG. 7). At 20 min post-injection (time 0), all rats received an injection of morphine (10 mg/kg, IV) and TFL tested 20, 40, 60, 90, 120, 150, 180, 210, 240, 360 and 480 min post-injection. Data are shown as actual TFL (sec) and as "maximum possible effect" (% MPE) using the formula, % MPE= [(post-injection TFL−baseline TFL)/(12−baseline TFL)]× 10023,35–38.

Antinociception Assessment by Paw Withdrawal Assay.
Hot-Plate Latency (HPL)

Figure 20:
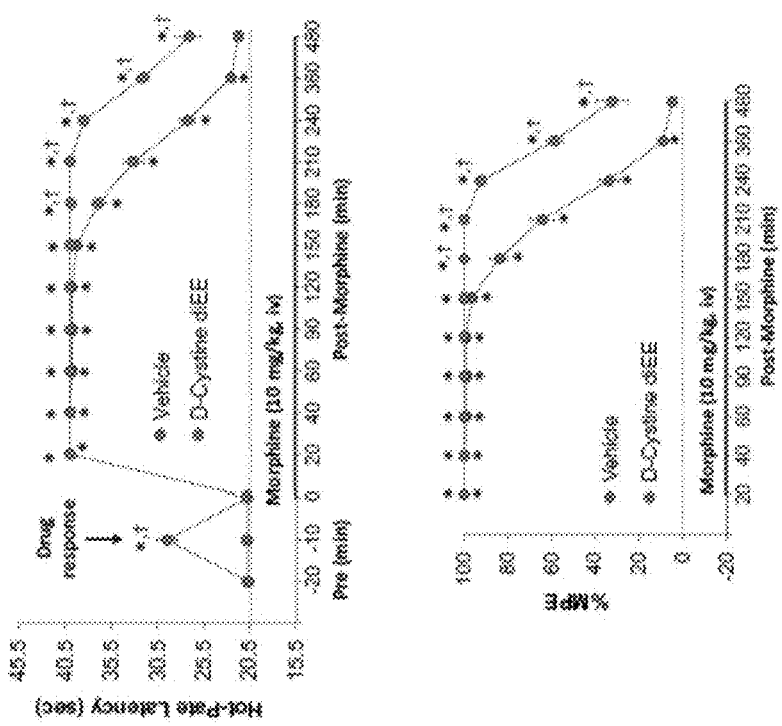
FIG. 20 illustrates plots showing changes in tail-flick latency (top panel) and hot-plate latency (bottom panel) elicited by injection of vehicle (VEH, saline) or d-cystine diethyl ester (d-cystine diEE, 500 μmol/kg, IV) and a subsequent injection of morphine (10 mg/kg, IV) in freely moving rats. The left-hand panels show actual data whereas the right-hand panels display the data as maximum possible effect (% MPE). The data are shown as mean±SEM. There were 9 rats in each group. *$P<0.05$, significant change from Pre. †$P<0.05$, d-cystine diEE versus vehicle.

The antinociceptive effects of morphine, vehicle and d-cystine diEE were assessed by hot-plate (hind-paw withdrawal) latency (HPL) test using the Hargreaves's test. In brief, paw withdrawal latency to a thermal stimulus was assessed using a radiant heat source (IITC, CA, USA) aimed at the planter surface of the left hind-paw. This method did not involve restraint while positioning the thermal stimulus sufficient enough to induce a latency of tail withdrawal of 20 s (baseline values) prior to injection of any drug (cut-off latency of 20 s was set to avoid tissue damage). Baseline HPL was tested in all rats (−20 min time-point in FIG. 20). One group of rats (80.3±0.6 days of age; 340±3 g body weight, n=9 rats) received an IV injection of vehicle (saline, 100 µL/100 g body weight) and the second group (80.0±0.5 days; 339±3 g, n=9 rats) received an injection of d-cystine diEE (500 µmol/kg, IV). HPL was tested in both groups 10 and 20 min later (−10 and 0 min in FIG. 20). At 20 min post-injection (time 0), all rats received an injection of morphine (10 mg/kg, IV) and HPL was tested 20, 40, 60, 90, 120, 150, 180, 210, 240, 360 and 480 min post-injection. Data are shown as actual HPL (sec) and as "maximum possible effect" (% MPE) using the formula, % MPE= [(post-injection HPL−baseline HPL)/(20−baseline HPL)]× 100.

Statistics

The recorded data (1 min bins) and derived parameters, Vt/Ti and Response Area (cumulative percent changes from pre-values) were taken for statistical analyses. The pre-drug 1 min bins excluded occasional marked deviations from resting due to movements or scratching by the rats. These exclusions ensured accurate determinations of baseline parameters. The data are presented as mean±SEM. All data unless other-wise stated (see immediately below) were analyzed by one-way or two-way analysis of variance followed by Student's modified t test with Bonferroni corrections for multiple comparisons between means using the error mean square terms from each ANOVA. A value of $P<0.05$ denoted the initial level of statistical significance that was modified according to the number of comparisons between means. The modified t-statistic is t=(mean group 1−mean group 2)/$[s\times(1/n_1+1/n_2)^{1/2}]$ where s2=the mean square within groups term from the ANOVA (the square root of this value is used in the modified t-statistic formula) and $n_1$ and $n_2$ are the number of rats in each group under comparison. Based on an elementary inequality called Bonferroni's inequality, a conservative critical value for the modified t-statistics taken from tables of t-distribution using a significance level of P/m, where m is the number of comparisons between groups to be performed. The degrees of freedom are those for the mean square for within group variation from the ANOVA table. In most cases, the critical Bonferroni value cannot be obtained from conventional tables of the t-distribution but may be approximated from widely available tables of the normal curve by $t^*=z+(z+z3)/4n$, with n being the degrees of freedom and z being the critical normal curve value for P/m. A value of $P<0.05$ was taken as the initial level of statistical significance. With respect to FIGS. 24-27, the data were analyzed by one-way ANOVA and Tukey's least significance difference (LSD) test, with statistical differences taken as $P<0.0540,41$.

Results

Ventilatory Parameters

Figure 14:
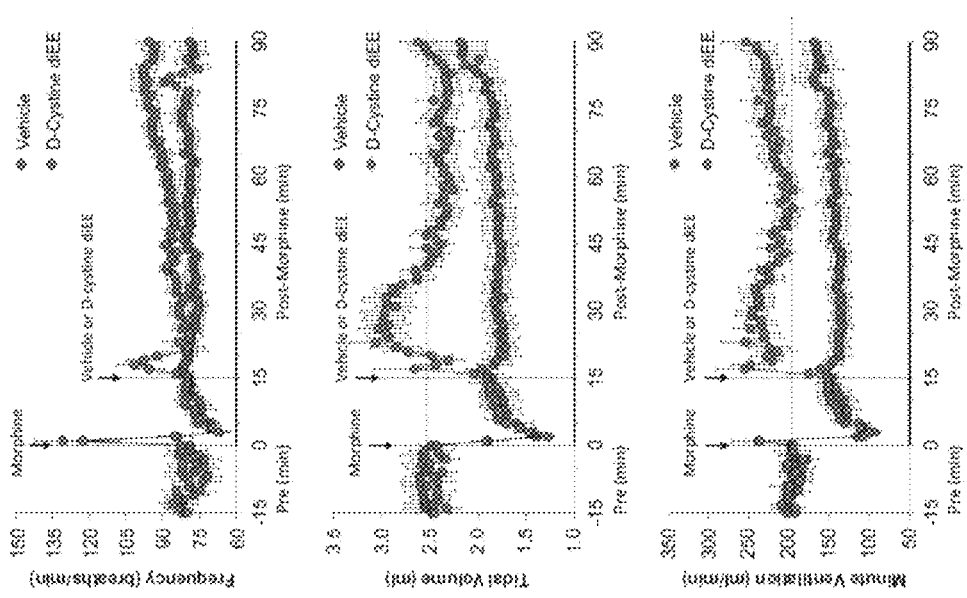
FIG. 14 illustrates plots showing changes in frequency of breathing (top panel), tidal volume (middle panel) and minute ventilation (bottom panel) in freely moving rats upon (a) injection of morphine (10 mg/kg, IV) and subsequent injection of vehicle (saline) or d-cystine diethyl ester (d-cystine diEE, 500 μmol/kg, IV). The data are presented as mean±SEM. There were 9 rats in each group.

The ages and body weights of the rats and their resting ventilatory parameters prior to the commencement of the whole-body plethysmography protocols are shown in Table 1. There were no between-group differences for any parameter ($P>0.05$, for all comparisons). A summary of the maximal initial responses elicited by morphine and the total effects recorded over the 15 min prior to the injection of d-cystine diEE are summarized in Table 2. The changes in frequency of breathing (Freq), tidal volume (TV) and minute ventilation (MV) upon injection of morphine (10 mg/kg, IV) and subsequent injection of vehicle or d-cystine diEE (500 μmol/kg, IV) are summarized in FIG. 14. The injection of morphine elicited a brief increase in Freq that was followed a relatively transient decrease that recovered before injection of vehicle of d-cystine diEE. Injection of vehicle did not elicit an immediate response in Freq, which remained at pre-injection values throughout the recording period. The injection of d-cystine diEE elicited a brief increase in Freq of about 5 min in duration that was followed by a gradual and sustained elevation in Freq. The injection of morphine elicited a prompt and sustained decrease in TV that was still pronounced at the time that vehicle of d-cystine diEE was given. Injection of vehicle did not affect TV, which gradually recovered to pre-injection levels toward the end of the recording period. As a result of the above changes in Freq and TV, it can be seen that morphine elicited a transient increase in MV that was followed by a sustained decrease and that d-cystine diEE elicited a prompt and long-lasting reversal of this effect of morphine.

Figure 15:
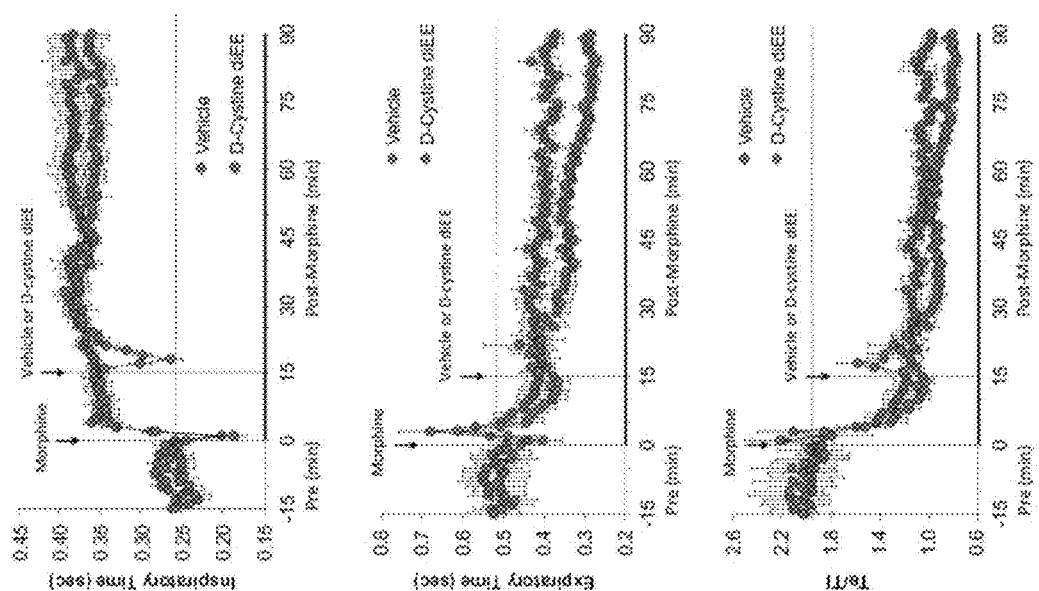
FIG. 15 illustrates plots showing changes in inspiratory time (top panel), expiratory time (middle panel) and expiratory time/inspiratory time (Te/Ti) (bottom panel) in freely moving rats upon (a) injection of morphine (10 mg/kg, IV) and subsequent injection of vehicle (saline) or D-cystine diethyl ester (D-cystine diEE, 500 μmol/kg, IV). The data are presented as mean±SEM. There were 9 rats in each group.

As summarized in FIG. 15, morphine elicited a transient decrease in Ti and Te that was followed by sustained increases in Ti and decreases in Te in rats that received vehicle 15 min after injection of morphine. The injection of d-cystine diEE elicited a brief decrease in Ti without greatly affecting Te. The long-lasting increase in Ti elicited by morphine was minimally smaller in d-cystine diEE-treated rats whereas the long-lasting decrease in Te was observably greater in the presence of d-cystine diEE. The ratio of Te/Ti fell markedly after the administration of morphine in the vehicle treated rats and similarly in the d-cystine diEE-treated rats.

Figure 16:
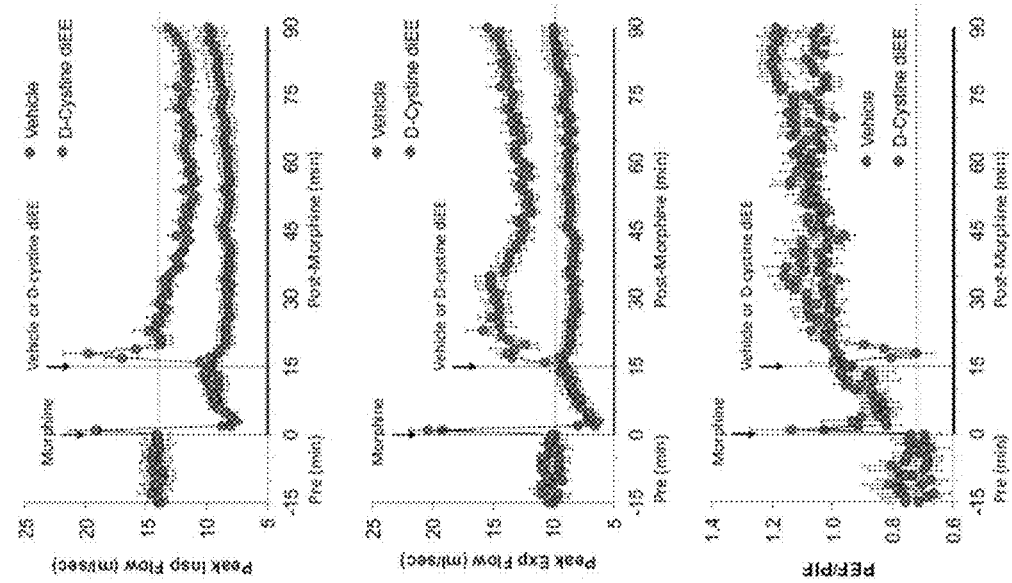
FIG. 16 illustrates plots showing changes in peak inspiratory flow (top panel), peak expiratory flow (middle panel) and peak expiratory flow/peak inspiratory flow (PEF/PIF) (bottom panel) in freely moving rats upon (a) injection of morphine (10 mg/kg, IV) and subsequent injection of vehicle (saline) or D-cystine diethyl ester (D-cystine diEE, 500 μmol/kg, IV). The data are presented as mean±SEM. There were 9 rats in each group.

FIG. 16 demonstrates that morphine elicited a pronounced and sustained decrease in PIF but lesser decreases in PEF in vehicle-treated rats. d-cystine diEE elicited a prompt and relatively sustained reversal of the effects of morphine on PIF and a marked increase in PEF to levels well above pre-morphine levels. Except for a decrease in PEF/PIF immediately upon injection of d-cystine diEE, the temporal changes in PEF/PIF elicited by morphine were similar in both groups.

FIG. 17 demonstrates that morphine elicited a sustained increase in $EF_{50}$ in rats that received vehicle. Administration of d-cystine diEE elicited a further prompt and sustained increase in $EF_{50}$ in morphine-treated rats. Morphine elicited a prompt and sustained decrease in inspiratory drive (TV/Ti) and relatively pronounced but shorter-lived decrease in expiratory drive (TV/Te). The injection of d-cystine diEE elicited a noticeable but partial recovery of inspiratory drive and a substantial and sustained increase in expiratory drive to well above pre-morphine levels.

The initial peak responses and the total responses elicited by vehicle or d-cystine diEE in morphine-treated rats are shown in FIG. 21. d-Cystine diEE elicited pronounced increases in Freq (along with a decrease in Ti but not Te, and an increase in Te/Ti), TV, MV, PIF and PEF (with a decrease in PE/PEF), $EF_{50}$, and inspiratory drive (TV/Ti and expiratory drive (TV/Te). In terms of the total response, d-cystine diEE elicited a relatively minor increase in Freq and decreases in Ti and Te, but robust sustained increases in TV, MV, PIF, PEF, PEF/PIF, $EF_{50}$ and in inspiratory drive and expiratory drives.

Figure 22:
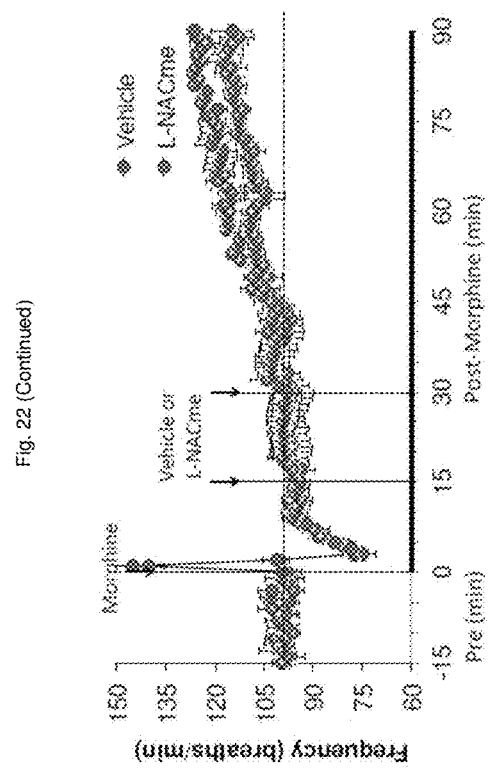
FIG. 22 illustrates plots showing changes in frequency of breathing (top panel), tidal volume (middle panel) and minute ventilation (bottom panel) in freely moving rats upon (a) injection of morphine (10 mg/kg, IV) and subsequent injection of vehicle (saline) or D-cystine (500 mol/kg, IV). The data are presented as mean±SEM. There were 9 rats in each group.
Figure 23:
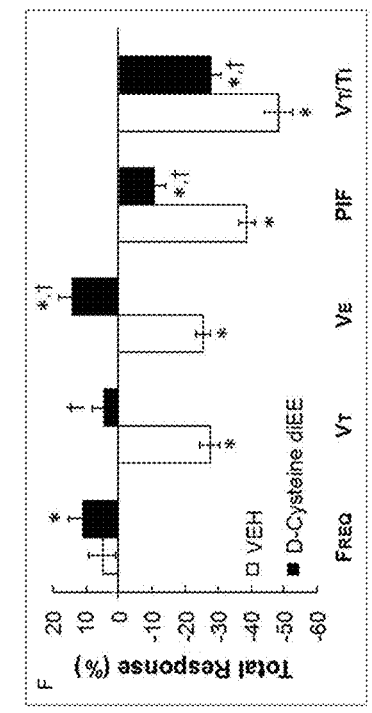
FIG. 23 illustrates plots showing changes in frequency of breathing (top panel), tidal volume (middle panel) and minute ventilation (bottom panel) in freely moving rats upon (a) injection of morphine (10 mg/kg, IV) and two subsequent injections of vehicle (saline) or N-acetyl-L-cysteine ethyl ester (L-NACme; 500 mol/kg, IV). The data are shown as mean±SEM. There were 9 rats in each group.

In contrast to d-cystine diEE, the injection of d-cystine (500 μmol/kg, IV) did not elicit immediate effects on Freq, TV or MV in morphine (10 mg/kg, IV)-treated rats although these parameters returned toward pre-morphine levels more quickly than in the vehicle-treated rats as seen in the last 15 min of the recording period (FIG. 22, Table 3. In addition, the injection of the potent reducing agent, l-NACme (2×500 μmol/kg, IV), elicited only minor effects on morphine (10 mg/kg, IV)-induced changes in Freq, TV and MV (FIG. 23, Table 3).

Blood-Gas Chemistry

Figure 18:
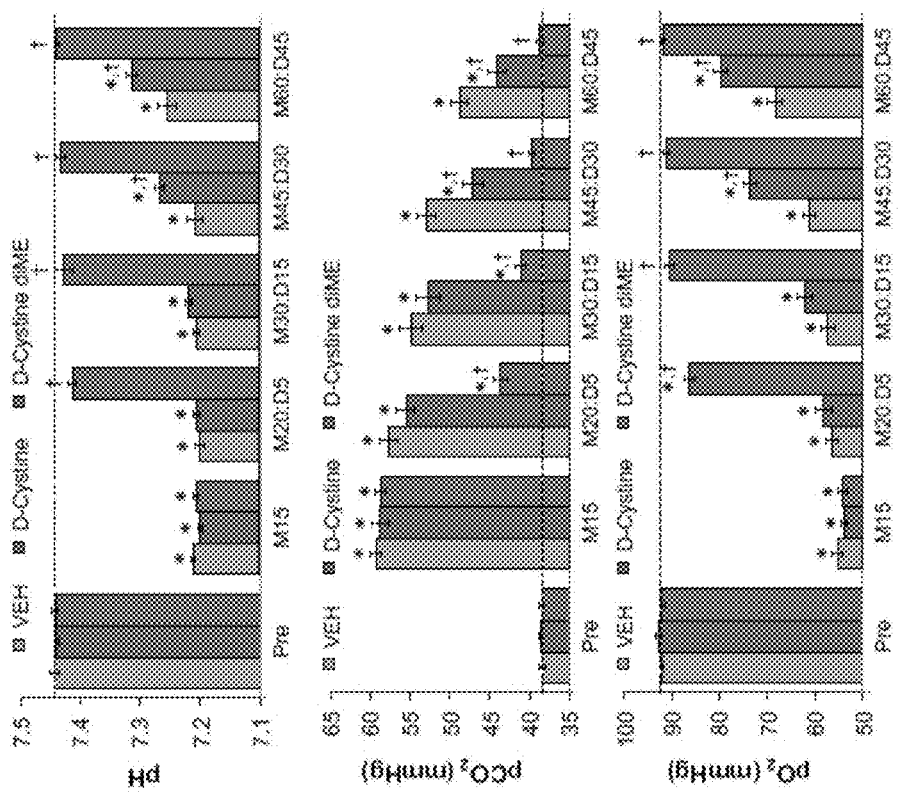
FIG. 18 illustrates graphs showing changes in pH, $pCO_2$, $pO_2$ and $sO_2$ elicited by injection of morphine (10 mg/kg, IV) in 3 separate groups of freely moving rats followed by injection of vehicle (VEH, saline), d-Cystine (500 μmol/kg, IV) or d-cystine dimethyl ester (d-cystine diME, 500 μmol/kg, IV). M15-M60, 15-60 min after injection of morphine. D5-D45, 5-45 min after injection of drug (vehicle, d-Cystine or d-cystine diME). The data are shown as mean±SEM. There were 9 rats in each group. *$P<0.05$, significant change from Pre-values. †$P<0.05$, d-cystine diEE versus vehicle.

The changes in pH, $pCO_2$, $pO_2$ and $sO_2$ elicited by injection of morphine (10 mg/kg, IV) in 3 separate groups of freely moving rats followed by injection of vehicle (VEH, saline), d-Cystine (500 μmol/kg, IV) or d-cystine diME (500 μmol/kg, IV) are summarized in FIG. 18. The M15-M60 term on each x-axis refers to 15-60 min after injection of morphine whereas D5-D45 refers to 5-45 min after injection of drug (vehicle, d-Cystine or d-cystine diME). Morphine elicited substantial falls in pH, $pO_2$ and $sO_2$ accompanied by substantial increases in $pCO_2$ (see time M15) Pre-values and responses to morphine were similar in the 3 groups. These values returned toward pre-injection after injection of vehicle. The values returned toward pre-injection levels faster after injection of d-cystine with these changes reaching significance at M45:D30 and M60:D45 time-points. The morphine-induced changes in ABG chemistry were reversed immediately (at M20:D5) by injection of d-cystine diME and this reversal was sustained throughout the experiment (at M60:D45). In contrast, the injection of d-cystine diME (500 μmol/kg, IV) elicited minimal immediate effects on Freq, TV and MV in morphine (10 mg/kg, IV)-treated rats.

Alveolar-Arterial Gradients

The changes in A-a gradients in the 3 groups of freely moving rats described under Blood-gas Chemistry elicited by morphine (10 mg/kg, IV) and then vehicle (VEH, saline), d-Cystine (500 μmol/kg, IV) or d-cystine diME (500 μmol/kg, IV) are shown in FIG. 19. Morphine elicited substantial and equivalent increases in $pCO_2$ in the 3 groups of rats (see time M15). These values did not return to pre-injection levels after injection of vehicle but returned toward pre-injection levels after injection of d-cystine, with these changes being significant at M45:D30 and M60:D45 times.

Morphine-induced increases in A-a gradient were reversed immediately (at M20:D5) by d-cystine diME and this reversal was sustained throughout the experiment (at M60:D45).

Antinociception Assays

The following experiments addressed the important issue as to whether the stereoisomeric configuration of cystine diME is a factor in any effects that this thiolester may have on the analgesic actions of morphine. We first tested the effects of d-cystine diME (500 µmol/kg, IV) or L-cystine diME (500 µmol/kg, IV) on analgesic status of adult male rats when given alone or when given in combination with morphine sulfate (1.0 mg/kg, IV) with testing performed between 20 to 30 min post-injection (FIGS. 14-27). In brief, neither d-cystine diME nor L-cystine diME affected thermal nociception (Hargreaves Testing—heat applied to a hind-paw) or mechanical allodynia (Von Frey Testing—pressure applied to a hind-paw) when given alone and neither thiolester affected the antinociception actions of morphine. However, we wanted to further explore whether d-cystine diME would affect a higher dose of morphine and to track the changes in antinociception status over a much longer time-course. Changes in tail-flick latencies (TFL, top panel) and hot-plate latencies (HPL, bottom panel) elicited by injection of vehicle or d-cystine diEE (500 µmol/kg, IV) and subsequent injection of morphine (10 mg/kg, IV) in freely moving male rats are summarized in FIG. 20. d-cystine diEE elicited a transient increase in TFL and HPL (both effects indicative of antinociception) that resolved within 15 min (time 0). The injection morphine elicited a pronounced increase in TFL and HPL of at least 4 h in duration in vehicle-treated rats. The antinociceptive effects of morphine were enhanced in d-cystine diEE-treated rats in that the maximal possible effect (% MPE) and duration of antinociception was greater than in vehicle-treated rats from 90 min after morphine injection. The antinociceptive effects of morphine were also enhanced by d-cystine (500 µmol/kg, IV) although to a lesser degree than by d-cystine diEE (Table 5).

Sedation

All rats that received morphine (10 mg/kg, IV) plus vehicle remained obviously sedated (they remained on their side not moving with their eyes closed) for at approximately 60 min, after which time they gradually recovered their footing and were able to groom and move about the chamber although full mobility was not evident for at least 2 h. Sedation in the rats that received morphine plus d-cystine diEE or d-cystine diME was indistinguishable from the rats the received morphine plus vehicle. The durations of the sedative and analgesic actions of morphine far exceeded the ventilatory depression elicited by the opioid (see FIGS. 14, 15, 16, 17, 18, 19, 20).

L-cystine diME

Figure 24:
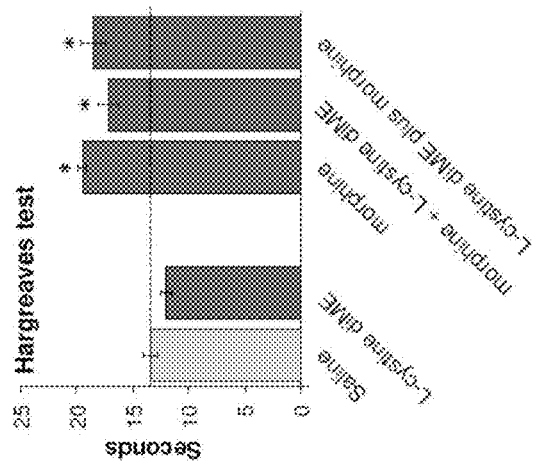
FIG. 24 illustrates a plot showing paw-withdrawal latencies (Hargreaves test) in rats pretreated with saline (n=8 rats), L-cystine diME (500 μmol/kg, IV; n=8 rats), morphine sulfate (1 mg/kg, IV, n=8 rats) and a combination of morphine plus L-cystine diME (n=6 rats) or L-cystine diME plus morphine (n=6 rats). The data are presented as mean±SEM. *P<0.05, morphine alone versus saline; morphine plus L-cystine diME and L-cystine diME plus morphine versus L-cystine diME alone.

Hargreaves Hind-paw Latency Test, see FIG. 24. We tested 8 rats for saline and L-cystine diME, and 6 rats each for morphine+L-cystine diME and L-cystine diME+morphine. The latencies (mean±SEM) in seconds for each treatment group are: Saline=13.4±0.7; L-cystine diME=12.0±0.5; morphine=19.5±0.4; morphine+L-cystine diME=17.2±0.9; L-cystine diME plus morphine=18.5±1.1. Morphine elicited a significant increase in withdrawal latency. The increases in latency elicited by morphine+L-cystine diME, and L-cystine diME+morphine were similar to those elicited by morphine alone (P>0.05, for both comparisons).

Figure 25:
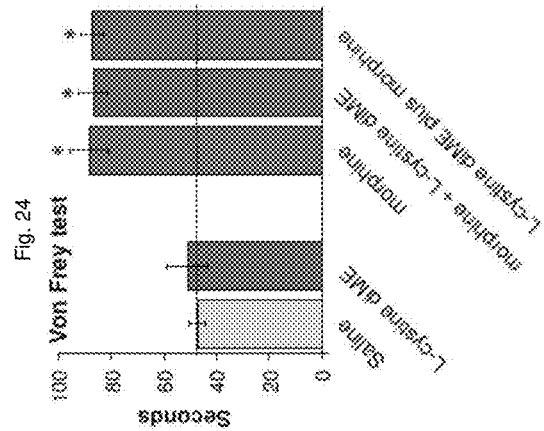
FIG. 25 illustrates a graph showing paw-withdrawal latencies (Von Frey test) in rats pretreated with saline (n=8 rats), L-cystine diME (500 μmol/kg, IV; n=8 rats), morphine (1 mg/kg, IV, n=8 rats) and a combination of morphine+L-cystine diME (n=6 rats) or L-cystine diME+morphine (n=6 rats). Data are presented as mean±SEM. *P<0.05, morphine alone versus saline; morphine+L-cystine diME or L-cystine diME+morphine versus L-cystine diME alone.

Von Frey Test, see FIG. 25. Using the same test groups above, we found that the forces (g) needed to initiate hind-paw withdrawal in each group was (mean±SEM): saline=47.4±3.3; L-Cystine diME=51.0±7.6; morphine=88.3±7.0; morphine+L-Cystine diME=86.9±5.2; L-Cystine diME+morphine=87.3±4.2. Morphine elicited a significant increase in withdrawal latency. The increases in latency elicited by morphine plus L-cystine diME, and L-cystine diME plus morphine were similar to those elicited by morphine alone (P>0.05, for both comparisons).

D-Cystine diME

Figure 26:
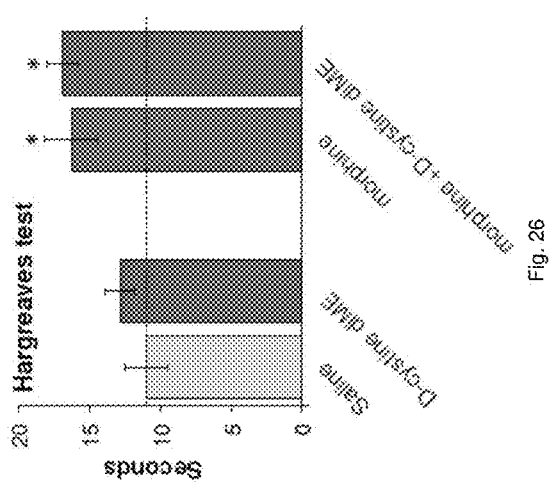
FIG. 26 illustrates a graph showing paw-withdrawal latencies (Hargreaves test) in rats pretreated with saline (n=3 rats), D-cystine diME (500 μmol/kg, IV; n=3 rats), morphine sulfate (1 mg/kg, IV, n=3 rats) and a combination of morphine+D-cystine diME (n=3 rats). The data are presented as mean±SEM. *P<0.05, morphine alone versus saline or morphine plus D-cystine diME versus L-cystine diME alone

Hargreaves Hind-paw Latency Test, see FIG. 26. We tested 3 rats for D-Cystine diME, 3 rats each for morphine alone and morphine+D-Cystine diME. The latencies (mean±SEM) in seconds for each treatment group were: saline=11.0±1.5; D-Cystine diME=12.9±1.0; Morphine=16.3±1.8; Morphine+D-Cystine diME=16.9±1.0. Using a repeated measures ANOVA and Tukey-Kramer (P<0.05 for significance and differences between and across trials) there was no significant difference across trials as well as no significant interaction between the trials and the drugs (P>0.05 for both). There was a significant drug effect (P<0.05). There was a significant difference between morphine and saline (P<0.001) as well as Morphine+D-Cystine diME and saline (P<0.01). There was not a significant difference between D-Cystine diME and saline (P>0.05). D-Cystine diME was significantly different from morphine (P<0.01), and significantly different from morphine+D-Cystine diME (P<0.05). Morphine and morphine+D-cystine diME was not different from each other (P>0.05).

Figure 27:
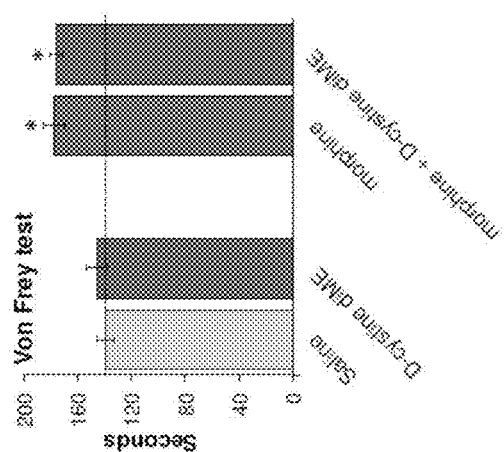
FIG. 27 illustrates a graph showing paw-withdrawal latencies (Von Frey test) in rats pretreated with saline (n=8 rats), D-cystine diME (500 μmol/kg, IV; n=3 rats), morphine (1 mg/kg, IV, n=10 rats) and a combination of morphine+ D-cystine diME (n=3 rats). Data are presented as mean±SEM. *P<0.05, morphine alone versus saline or morphine+D-cystine diME versus L-cystine diME alone.

Von Frey Test, see FIG. 27. Using the same test groups, 8 rats for saline, 3 rats for D-cystine diME, 3 rats for morphine+D-cystine diME, and 10 for Morphine alone, we found that force (in grams) needed to initiate hind-paw withdrawal was (mean±SEM): Saline=139±7; D-cystine diME=144±8; Morphine=177±8; Morphine+D-cystine diME=176±5. Saline D-cystine diME values were similar to one another (P>0.05). Morphine alone and morphine+D-cystine diME were significantly different from saline or D-cystine diME alone (P<0.001 for both comparisons). The morphine values and morphine+D-cystine diME values were similar to one another (P>0.05).

This example demonstrates that the systemic injection of d-cystine diEE or d-cystine diME elicit an immediate and sustained reversal of the negative effects of a 10 mg/kg dose of morphine on ventilatory parameters, gas exchange in the lungs (elevated A-a gradient) and ABG chemistry in unanesthetized adult male Sprague-Dawley rats without (apparently) affecting the sedative effects of morphine and while augmenting the antinociceptive effects of the opioid. The major findings with respect to potential clinical impact are clearly that d-cystine diEE or d-cystine diME reversed the negative effects of morphine on MV and ABG chemistry, effects that would be the major contributors to restoration of ventilatory performance. The ability of d-cystine diEE or d-cystine diME to reverse the other effects of morphine such as depression of PIF, while important must be considered secondary to the effects on MV and especially the TV component. Taken together, it would appear unlikely that d-cystine diEE or d-cystine diME directly modulate the pharmacological actions of morphine by competitive or non-competitive blockade of opioid receptors since all of the above effects of morphine are antagonized by opioid receptor antagonists such as naloxone and naltrexone. The site(s) of action and molecular mechanisms by which d-cystine diEE or d-cystine diME exert their robust effects on ventilatory parameters, A-a gradient and ABG chemistry in morphine-treated rats while augmenting the antinociceptive effects of the opioid, remain to be determined. Evidence that morphine blocks the entry of l-cysteine into neurons via inhibition of EAA36,7 raises the possibility that either (a) a decrease in intracellular levels of 1-cysteine and resulting enhancement of the oxidative (less reductive) status of the cell and/or (b) loss of participation of 1-cysteine in a myriad of intracellular metabolic pathways including the generation of the gaseous neurotransmitter hydrogen sulfide, plays a role in the deleterious actions of morphine while conversely promoting the antinociceptive and sedative actions of the opioid. The potent actions of d-cystine diEE, d-cystine diME and 1-cysteine ethyl ester on the negative effects of morphine on ventilation and gas-exchange support these concepts whereas the ability of the thiolesters to augment the antinociceptive actions of morphine does not. Transport of cystine esters into the cell would not itself correct for the loss of sulfhydryl equivalents since cystine is already in the more oxidized disulfide state, and d-cystine or D-cysteine would not participate in most of the metabolic pathways of 1-cysteine, but uptake of d-cystine esters could potentially drive up levels of intracellular 1-cysteine. However, our finding that the highly cell-permeable thiolester reducing agent, N-acetyl-1-cysteine methyl ester21, had minimal effects on the ventilatory depressant effects of morphine suggests that d-cystine diEE and d-cystine diME do not act simply by increasing reducing equivalents in cells. Potential mechanisms of action of d-cystine diEE and d-cystine diME may involve (a) interference with opioid receptor-linked (3-arrestin cell signaling, which would spare the G protein-mediated antinociceptive actions of morphine, and/or conversion of these thiolesters to bioactive S-nitrosothiols (i.e., S-nitroso-d-cystine diEE, S-nitroso-d-cystine diME) that may act as intracellular nitrosating agents similar to S-nitroso-1-cysteine ethyl ester. S-nitrosothiols in the brainstem, peripheral structures and red blood cells play important roles in ventilatory control processes. For example, microinjection of S-nitrosothiols into the nucleus tractus solitarius elicit robust increases in MV54 as do systemic delivery of S-nitrosothiols to the carotid bodies. Our evidence that S-nitrosothiols such as S-nitroso-1-cysteine exert their ventilatory effects via direct modulation of voltage-gated K+-channels may represent a molecular target for d-cystine diEE and d-cystine diME and their S-nitrosothiol forms, which may target the intracellular domains of these channels.

As shown previously, the 10 mg/kg dose of morphine elicited only a transient decrease in Freq. This apparent lack of sustained effects on Freq is misleading in the sense that morphine elicited a profound and sustained increase in Ti and a sustained decrease in Te (present study). Despite evidence that the depressant effects of morphine on Freq involve suppression of carotid body chemoreceptor reflexes, we reported that the ventilatory depressant effects of morphine (10 mg/kg, IV) in freely moving rats were exacerbated in rats with bilateral carotid sinus nerve transection, suggesting that morphine does not directly affect or potentially pro-motes carotid body chemoreflexes in these unanesthetized rats. d-cystine diEE had minor effects on the actions of morphine on the above parameters (i.e., Freq rose to higher levels than in vehicle-treated rats, whereas Ti did not rise as much and Te deceased to a greater extent). It would seem that the carotid body may not be a major site of direct action considering the minimal effects of the thiolester on Freq.

The first novel set of findings in the present example was that d-cystine diEE elicited an immediate and sustained reversal of the negative effects of morphine on TV (and therefore MV), PIF, PEF, and inspiratory and expiratory drives, while promoting the enhancing the effects of morphine on $EF_{50}$. In contrast, the injection of the parent thiol, d-cystine, did not elicit immediate responses in morphine-treated rats, although Freq, TV and MV (and other variables, data not shown) returned to pre-morphine levels somewhat more rapidly than in vehicle-injected rats. The second novel set of findings was that d-cystine diME elicited an immediate and sustained reversal of the negative effects of morphine on ABG chemistry whereas d-cystine produced a gradual recovery that was greater than in vehicle-injected rats. This is related to the third novel finding that d-cystine diME elicited a prompt and sustained reversal of the negative effects of morphine on gas-exchange within the lungs (as defined by reversal of the morphine-induced increase in A-a gradient) whereas again, d-cystine promoted the recovery of the effects of morphine from about 30 min after the injection of the thiolester (45 min post-morphine). Taken together, the ability of d-cystine diEE/diME to reverse the above negative effects of morphine is due to a unique profile of activity that also includes potentiation of the antinociceptive actions of the opioid. With respect to antinociception, the ability of systemically injected d-cystine diEE to elicit a transient antinociception (as detected by both TF and HP assays) is consistent to a degree with evidence that direct injection of d-cystine into the hind-paw of rats elicited profound blockade of thermal nociception. d-cystine may exert its effects on nociceptive processing via redox modulation (closure) of ion-channels such as T-type voltage-gated $Ca^{2+}$ channels.

The gradual appearance of effects of d-cystine on morphine-induced changes in ventilatory parameters, ABG chemistry, A-gradient and TFL raises the possibility that d-cystine diEE and d-cystine diME exert their effects via rapid introduction of d-cystine into cells as opposed to gradual entry of d-cystine through uptake systems. The uptake of L-cystine into cells is mediated by the cystine-glutamate antiporter system xc- and the Na+-independent high-affinity cystine transporter, b0, +A. There is evidence that cystine-glutamate antiporter system xc-does not transport d-cystine and to our knowledge it is not known whether d-cystine is transported by b0, +AT. As such, the mechanisms (e.g., facilitated entry via transporters, conversion to other compounds which gain cell entry or act on membrane proteins), by which d-cystine exerts its latent effects remain unknown, but are worthy of examination.

We show that d-cystine diEE, d-cystine diME and to a lesser degree, d-cystine itself, represent a novel class of compounds that have an important therapeutic profile that may be of value in the clinic to treat opioid-induced respiratory depression without compromising antinociception. Taken together, it is evident that d-cystine diEE and d-cystine diME are able to impair some of the actions of morphine (i.e., OIRD) but not others (i.e., antinociception, sedation). It would therefore appear that the thiolesters do not directly interfere with opioid receptors but that the delivery of thiolesters to neurons participating in OIRD may differentially affect the signaling processes (e.g., G protein- and β-arrestin-dependent) that mediate the effects of morphine on breathing. The positive results of d-cystine diEE against morphine in the ventilation (plethysmography) studies coupled to the positive effects of d-cystine diME against morphine in the ABG chemistry and A-a gradient studies would suggest that while the presence of an ester linkage is vital to cell penetration, whether this linkage is an ethyl ester or methyl ester may not be a key determinant of bioactivity against morphine. In addition, the lack of effect of the powerful reducing agent 1-NACme on morphine-induced respiratory depression would tentatively argue that the effects of d-cystine diEE and d-cystine diME are not simply due to the breakdown of the disulfide esters into the monothiol (reduced) forms, which then exert their intracellular actions as reducing agents.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of attenuating opioid induced ventilatory and/or respiratory depression and/or augmenting opioid induced analgesia in a subject in need thereof, the method comprising:
    administering to the subject an opioid in combination with a therapeutically effective amount of a composition comprising a cystine ester or an adduct, a pharmaceutically acceptable salt, a tautomer, or a solvate thereof.
2. The method of claim 1, wherein the therapeutically effective amount is an amount effective to stimulate the ventilatory and/or respiratory drive of the subject and/or augment opioid induced analgesia.
3. The method of claim 1, wherein the cystine ester has the formula:

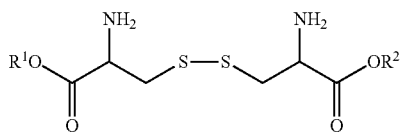

where $R^1$ and $R^2$ are the same or different and are selected from the group consisting of H, unsubstituted or substituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl, and heterocyclyl containing from 5-14 ring atoms, wherein at least one of $R^1$ and $R^2$ is not a H; or an adduct, a pharmaceutically acceptable salt, a tautomer, or a solvate thereof.

4. The method of claim 3, wherein $R^1$ and $R^2$ are independently H or an unsubstituted or substituted $C_1$-$C_{24}$ alkyl, wherein at least one of $R^1$ and $R^2$ is not a H.

5. The method of claim 3, wherein $R^1$ and $R^2$ are independently selected from the group consisting of H, methyl, ethyl, propyl, and butyl, wherein at least one of $R^1$ and $R^2$ is not a H.
6. The method of claim 1, wherein the cystine ester is a cystine dialkyl ester.
7. The method of claim 6, wherein the cystine dialkyl ester is a D-cystine dialkyl ester or an adduct, a pharmaceutically acceptable salt, a tautomer, or a solvate thereof.
8. The method of claim 6, wherein the cystine dialkyl ester is selected from the group consisting of cystine dimethyl ester, cystine diethyl ester, combinations thereof, or an adduct, a pharmaceutically acceptable salt, a tautomer, or a solvate thereof.
9. The method of claim 6 wherein the cystine dialkyl ester is D-cystine dimethyl ester or an adduct, a pharmaceutically acceptable salt, a tautomer, or a solvate thereof.
10. The method of claim 1, wherein the opioid comprises at least one of alfentanil, buprenorphine, butorphanol, carfentanil, codeine, diamorphine, dextromoramide, dezocine, dihydrocodeine, fentanyl, hydrocodone, hydromorphone, levorphanol, meperidine, meptazinol, methadone, morphine, nalbuphine, nalorphine, opium, oxycodone, oxymorphone, pentazocine, propoxyphene, remifentanil, sufentanil, tapentadol, and tramadol, and pharmaceutically acceptable salts thereof.
11. The method of claim 1, wherein opioid administration elicits disturbances in ventilatory parameters, ABG chemistry, and A-a gradient while causing sedation and analgesia.
12. The method of claim 11, wherein the therapeutically effective amount of the composition administered to the subject is the amount effective to elicit sustained reversal of opioid elicited disturbances in ventilatory parameters, ABG chemistry, and A-a gradient while augmenting opioid induced sedation and/or analgesia.
13. The method of claim 1, wherein the composition is administered to the subject systemically.
14. The method of claim 1, wherein the opioid is administered systemically by intravenous infusion.
15. The method of claim 1, wherein the composition is administered concurrently with opioid administration and/or up to about 120 minutes before or after initiation of opioid administration.
16. The method of claim 1, wherein the opioid comprises morphine and/or fentanyl.

* * * * *